US010583286B2

(12) United States Patent
Swanson et al.

(10) Patent No.: US 10,583,286 B2
(45) Date of Patent: Mar. 10, 2020

(54) METHODS AND DEVICES FOR NEUROMODULATION OF THE ADRENAL GLAND

(71) Applicant: Boston Scientific Neuromodulation Corporation, Valencia, CA (US)

(72) Inventors: Lynne E. Swanson, Edina, MN (US); William C. Stoffregen, Lake Elmo, MN (US); Bryan A. Clark, Forest Lake, MN (US); Michael X. Govea, Castaic, CA (US); Dennis B. Werner, Big Lake, MN (US); Natalie A. Brill, Sherman Oaks, CA (US); Pramodsingh H. Thakur, Woodbury, MN (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 57 days.

(21) Appl. No.: 15/847,561

(22) Filed: Dec. 19, 2017

(65) Prior Publication Data
US 2018/0104480 A1  Apr. 19, 2018

Related U.S. Application Data

(63) Continuation-in-part of application No. 15/683,750, filed on Aug. 22, 2017, now Pat. No. 10,441,788.
(Continued)

(51) Int. Cl.
*A61N 1/36* (2006.01)
*A61B 5/11* (2006.01)
(Continued)

(52) U.S. Cl.
CPC ............ *A61N 1/0556* (2013.01); *A61B 5/021* (2013.01); *A61B 5/1118* (2013.01);
(Continued)

(58) Field of Classification Search
CPC ................ A61N 1/0556; A61N 1/0558; A61N 1/36031; A61N 1/36139; A61N 1/3606;
(Continued)

(56) References Cited

U.S. PATENT DOCUMENTS

2003/0216792 A1  11/2003 Levin et al.
2004/0049240 A1  3/2004 Gerber et al.
(Continued)

FOREIGN PATENT DOCUMENTS

EP  2437848 A1  4/2012

OTHER PUBLICATIONS

Kanczkowski et al., "Adrenal Gland Microenvironment and Its Involvement in the Regulation of Stress-Induced Hormone Secretion during Sepsis", (Dec. 14, 2016), frontiers in Endocrinology, vol. 7, Article 156, pp. 1-9. (Year: 2016).*
(Continued)

*Primary Examiner* — Catherine M Voorhees
(74) *Attorney, Agent, or Firm* — Lowe Graham Jones PLLC; Bruce E. Black

(57) ABSTRACT

Aspects of the present disclosure are directed toward apparatuses, systems, and methods for delivering therapy to an adrenal gland of a patient. The apparatuses, systems, and methods may include a housing and a plurality of electrodes arranged with the housing. In addition, one or more of the plurality of electrodes may deliver stimulation energy to modulate L-dopa release.

11 Claims, 11 Drawing Sheets

Related U.S. Application Data

(60) Provisional application No. 62/378,419, filed on Aug. 23, 2016.

(51) Int. Cl.
| | | |
|---|---|---|
| A61B 5/00 | (2006.01) | |
| A61N 1/05 | (2006.01) | |
| A61B 5/021 | (2006.01) | |
| A61F 7/12 | (2006.01) | |
| A61F 7/00 | (2006.01) | |

(52) U.S. Cl.
CPC .......... *A61B 5/4227* (2013.01); *A61B 5/4836* (2013.01); *A61N 1/3606* (2013.01); *A61N 1/36031* (2017.08); *A61N 1/36139* (2013.01); *A61B 5/02125* (2013.01); *A61B 2562/0219* (2013.01); *A61F 7/12* (2013.01); *A61F 2007/0075* (2013.01); *A61F 2007/126* (2013.01); *A61N 1/0553* (2013.01); *A61N 1/0558* (2013.01); *A61N 1/36171* (2013.01); *A61N 1/36175* (2013.01)

(58) Field of Classification Search
CPC ............ A61N 1/36175; A61N 1/36171; A61N 1/0553; A61B 5/021; A61B 5/1118; A61B 5/4836; A61B 5/4227; A61B 2562/0219; A61B 5/02125; A61F 2007/126; A61F 2007/0075; A61F 7/12
See application file for complete search history.

(56) References Cited

U.S. PATENT DOCUMENTS

| | | | | |
|---|---|---|---|---|
| 2005/0065562 | A1* | 3/2005 | Rezai | A61N 1/05 607/9 |
| 2006/0116721 | A1* | 6/2006 | Yun | A61N 1/3605 607/2 |
| 2006/0195157 | A1 | 8/2006 | Lee et al. | |
| 2009/0192558 | A1 | 7/2009 | Whitehurst et al. | |
| 2010/0185249 | A1 | 7/2010 | Wingeier et al. | |
| 2010/0305664 | A1* | 12/2010 | Wingeier | A61N 1/36007 607/62 |
| 2010/0312305 | A1* | 12/2010 | Leiter | A61B 5/4094 607/45 |
| 2011/0160793 | A1 | 6/2011 | Gindele | |
| 2014/0162933 | A1* | 6/2014 | Hatchwell | C12Q 1/6883 514/1.1 |
| 2015/0142083 | A1 | 5/2015 | Yomtov | |
| 2015/0148878 | A1 | 5/2015 | Yoo et al. | |
| 2015/0251008 | A1 | 9/2015 | Rezai et al. | |
| 2016/0038749 | A1* | 2/2016 | Maile | A61N 1/37217 607/4 |
| 2017/0106185 | A1 | 4/2017 | Orts et al. | |
| 2018/0056062 | A1 | 3/2018 | Swanson et al. | |
| 2018/0056071 | A1 | 3/2018 | Swanson et al. | |
| 2019/0169576 | A1* | 6/2019 | Jo | C12N 5/0619 |

OTHER PUBLICATIONS

Edwards, A. V. "Adrenal Catecholamine Output in Response to Stimulation of the Splanchnic Nerve in Bursts in the Conscious Calf." J. Physiol., 327:409-419, 1982.

Foucart, Sylvain; et al. "Local Modulation of Adrenal Catecholamines Release by Beta-2 Adrenoceptors in the Anaesthetized Dog." Naunyn-Schmiedeberg's Arch Pharmacol, 337:29-34, 1988.

Gaspo, Rania; et al. "Correlation Between Neural Release of VIP and Adrenomedullary Catecholamine Secretion in Vivo." American Journal of Physiology—Regulatory, Integrative and Comparative Physiology, 268(6):R1449-R1455, Jun. 1, 1995.

Greenway, Clive V. and Innes, Rome I. "Effects of Splanchnic Nerve Stimulation on Cardiac Preload, Afterload, and Output in Cats." Journal of the American Heart Association, Circulation Research, 46(2):181-189, Feb. 1980.

Grynszpan-Winograd, Odile. "Adrenaline and Noradrenaline Cells in the Adrenal Medulla of the Hamster: A Morphological Study of Their Innervation." Journal of Neurocytology 3:341-361, 1974.

Ii-Vi Marlow. "How Do Thermoelectric Coolers (TEC) Work?" [online], [retrieved Mar. 8, 2018, available at least as early as Apr. 7, 2016]. Retrieved from the Internet <https://www.marlow.com/how-do-thermoelectric-coolers-tecs-work>, 4 pages.

International Search Report and Written Opinion issued in PCT/US2017/048086, dated Nov. 7, 2017, 12 pages.

International Search Report and Written Opinion issued in PCT/US2017/048088, dated Dec. 5, 2017, 14 pages.

Janssens, Karin A. M.; et al. "Mood and Anxiety Disorders in Chronic Fatigue Syndrome, Fibromyalgia, and Irritable Bowel Syndrome: Results From the LifeLines Cohort Study." Psychosomatic Medicine, V77:449-457, May 2015.

Klevans, Larry R. and Gebber, Gerard L. "Comparison of Differential Secretion of Adrenal Catecholamines by Splanchnic Nerve Stimulation and Cholinergic Agents." The Journal of Pharmacology and Experimental Therapeutics, 1970, 172(1):69-76.

Klimas, Nancy G.; et al. "Biomarkers for Chronic Fatigue." HHS Public Access, Brain Behav. Immun., Author Manuscript, Available in PMC Mar. 30, 2017, pp. 1-22.

Morrison, Shaun F.; et al. "Different Adrenal Sympathetic Preganglionic Neurons Regulate Epinephrine and Norepinephrine Secretion." Am J. Regulatory Integrative Comp. Physiol., 279:R1763-R1775, 2000.

Perlman, Robert L.; et al. "Catecholamine Release From the Adrenal Medulla." Clinics in Endocrinology and Metabolism, 6(3):551-576, Nov. 1977.

Peroutka, Stephen. "Migraine: A Chronic Sympathetic Nervous System Disorder." Headache, Views and Perspectives, 44:53-64, 2004.

Schatzberg, Alan F.; et al. "Psychotic and Nonpsychotic Depressions: II. Platelet MAO Activity, Plasma Catecholamines, Cortisol, and Specific Symptoms." Psychiatry Research, 20:155-164, 1986.

Shimazu, Takeshi; et al. "Regulation of Glycogen Metabolism in Liver by the Autonomic Nervous System. III Differential Effects of Sympathetic-Nerve Stimulation and of Catecholamines on Liver Phosphorylase." Biochimica Et Biophysica Acta, BBA 26024, 165:349-356, 1968.

Siddiqi, Shan H.; et al. "The Human Experience With Intravenous Levodopa." Frontiers in Pharmacology, Review, vol. 6, Article 307, pp. 1-22, Jan. 2016.

Strahler, Jana; et al. "Norepinephrine and Epinephrine Responses to Physiological and Pharmacological Stimulation in Chronic Fatigue Syndrome." Biological Psychology 94:160-166, 2013.

Vlainich, Roberto; et al. "Effect of Intravenous Lidocaine Associated With Amitriptyline on Pain Relief and Plasma Serotonin, Norepinephrine, and Dopamine Concentrations in Fibromyalgia." Clin J Pain, 27(4):285-288, 2011.

Vollmer, Regis R.; et al. "Selective Activation of Norepinephrine- and Epinephrine-Secreting Chromaffin Cells in Rat Adrenal Medulla." American Physiological Society, 1992, R716-R721.

Wakade, Arun R. and Wakade, Taruna D. "Secretion of Catecholamines From Adrenal Gland by a Single Electrical.Shock: Electronic Depolarization of Medullary Cell Membrane." Proc. Natl. Acad. Sci. USA, vol. 79, pp. 3071-3074, May 1982.

International Preliminary Report on Patentability issued in PCT/US2017/048086, dated Mar. 7, 2019, 7 pages.

International Preliminary Report on Patentability issued in PCT/US2017/048088, dated Mar. 7, 2019, 8 pages.

International Search Report and Written Opinion issued in PCT/US2018/066417, dated Mar. 18, 2019, 28 pages.

* cited by examiner

METHODS AND DEVICES FOR NEUROMODULATION OF THE ADRENAL GLAND

CROSS-REFERENCE TO RELATED APPLICATION

This application is a continuation-in-part of U.S. application Ser. No. 15/683,750, filed Aug. 22, 2017, which claims priority to Provisional Application No. 62/378,419, filed Aug. 23, 2016, all of which are herein incorporated by reference in their entirety.

TECHNICAL FIELD

The present disclosure relates to medical devices and methods for providing stimulation therapy. More specifically, the disclosure relates to devices and methods for delivering therapy to an adrenal gland of a patient.

BACKGROUND

Electrical stimulation may be therapeutic in a variety of diseases and disorders. Leads used in electrical stimulation may be implanted within, adjacent to, or near a targeted area. In certain instances, the lead or leads may be arranged near nerves, muscles, or other tissue.

Dysfunction of the adrenomedullary system, or abnormal levels of catecholamines, such as norepinephrine, epinephrine and dopamine, have been associated with symptoms including depression, fibromyalgia, chronic fatigue, chronic pain, migraines, orthostatic intolerance, Postural Orthostatic Tachycardia Syndrome (POTS), and other disease states. In addition, abnormal levels of L-dopa have been associated with degenerative diseases such as Parkinson's disease. Stimulation of the adrenal gland can release or block the release of catecholamines and/or modulate release of L-dopa directly into the bloodstream.

Preganglionic sympathetic axons of the splanchnic nerve terminate at chromaffin cells in the medulla of the adrenal glands. Two populations of chromaffin cells, one releasing epinephrine and one norepinephrine, demonstrate different innervation patterns. As a result, different stimulation patterns may be used to alter these levels independently to drive the abnormal levels of catecholamines toward normal levels thereby providing therapy and/or treatment for one or more of the various disease states associated therewith.

SUMMARY

In Example 1, an apparatus for delivering therapy to an adrenal gland of a patient, the apparatus including: a housing configured to attach to a portion of the adrenal gland of the patient; and a plurality of stimulation elements arranged with the housing, the plurality of electrodes being configured to deliver stimulation energy through at least one of the plurality of electrodes to modulate release of L-dopa into a bloodstream of the patient.

In Example 2, the apparatus of Example 1, wherein the plurality of stimulation elements are configured to stimulate the adrenal gland and release of L-dopa into the blood stream to maintain dopamine levels of the patient within a zone.

In Example 3, the apparatus of Example 1, wherein the housing is a leadless body housing configured to engage the portion of the adrenal gland.

In Example 4, the apparatus of Example 1, wherein the housing is a lead body configured to engage the portion of the adrenal gland.

In Example 5, the apparatus of Example 1, wherein the plurality of stimulation elements are configured to deliver at least one of electrical stimulation, light stimulation, sound stimulation, thermal stimulation, and magnetic stimulation to the adrenal gland to modulate the release of L-dopa.

In Example 6, the apparatus of Example 1, further including a sensor configured to measure the L-dopa levels within the patient and alter the stimulation energy delivered through the at least one of the plurality of stimulation elements to maintain the L-dopa release within a zone.

In Example 7, the apparatus of Example 6, wherein the sensor is at least one of a vascular sensor configured to measure hypotension, a sensor configured to measure blood pressure of the patient, a bioimpedence sensor configured to measure blood pressure of the patient, an electoral sensor configured to assess vascular tone or heart pulse transit time, an optical sensor configured to assess vascular tone or heart pulse transit time, and an accelerometer configured to measure physical movement of the patient.

In Example 8, the apparatus of Example 7, wherein the housing includes a communications component configured to communicate wireless signals, and the sensor is configured to measure the dopamine levels associated with L-dopa within the patient and communicate feedback to the communications component via wireless signals to alter the stimulation energy delivered through the at least one of the plurality of stimulation elements to maintain the L-dopa release within a zone.

In Example 9, the apparatus of Example 1, wherein the plurality of stimulation elements are configured to delivery stimulation energy on a duty cycle based on a metabolization time of L-dopa within the patient.

In Example 10, the apparatus of Example 1, wherein the delivery of stimulation energy modulates release of L-dopa to lessen at least one of tremors, muscle rigidity, and bradykinesia of the patient.

In Example 11, the apparatus of Example 1, wherein the plurality of stimulation elements are configured to intermittently or continuously instruct delivery of the stimulation energy through the plurality of electrodes.

In Example 12 a system for delivering therapy to an adrenal gland of a patient, the system including: a housing configured to attach to a portion of the adrenal gland of the patient; a plurality of stimulation elements arranged with the housing, the plurality of electrodes being configured to deliver stimulation energy through at least one of the plurality of electrodes to modulate release of L-dopa into a bloodstream of the patient; and a sensor configured to measure dopamine levels within the patient associated with the L-dopa release and alter the stimulation energy delivered through the at least one of the plurality of stimulation elements in response thereto.

In Example 13, the system of Example 12, wherein the sensor is at least one of a vascular sensor configured to measure hypotension, a sensor configured to measure blood pressure of the patient, a bioimpedence sensor configured to measure blood pressure of the patient, an electoral sensor configured to assess vascular tone or heart pulse transit time, an optical sensor configured to assess vascular tone or heart pulse transit time, and an accelerometer configured to measure physical movement of the patient.

In Example 14, the system of Example 12, wherein the sensor is configured to measure a physical symptom of the patient associated with Parkinson's disease.

In Example 15, the system of Example 12, wherein the controller is further configured to instruct delivery of the stimulation energy through the at least one of the plurality of electrodes at a frequency between 2 Hz and 20 kHz.

In Example 16, the system of Example 12, wherein the plurality of stimulation elements are configured to stimulate the adrenal gland and release of L-dopa into the blood stream to maintain dopamine levels of the patient within a zone In Example 17, a method of delivering therapy to an adrenal gland of a patient, the method including: delivering a housing to a portion of the adrenal gland of the patient, the housing including a plurality of stimulation elements arranged with the housing; and delivering stimulation energy through at least one of a plurality of electrodes leadless implantable medical to modulate aldosterone levels within the patient.

In Example 18, the method of Example 17, further including delivering stimulation energy to peripheral sympathetic nerves to modulate the release of L-dopa into the bloodstream.

In Example 19, the method of Example 17, further including delivering deep brain stimulation energy to the patient delivering stimulation energy.

In Example 20, the method of Example 17, further including measuring a physical symptom of the patient associated with Parkinson's disease and altering delivery of the stimulation in response thereto.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
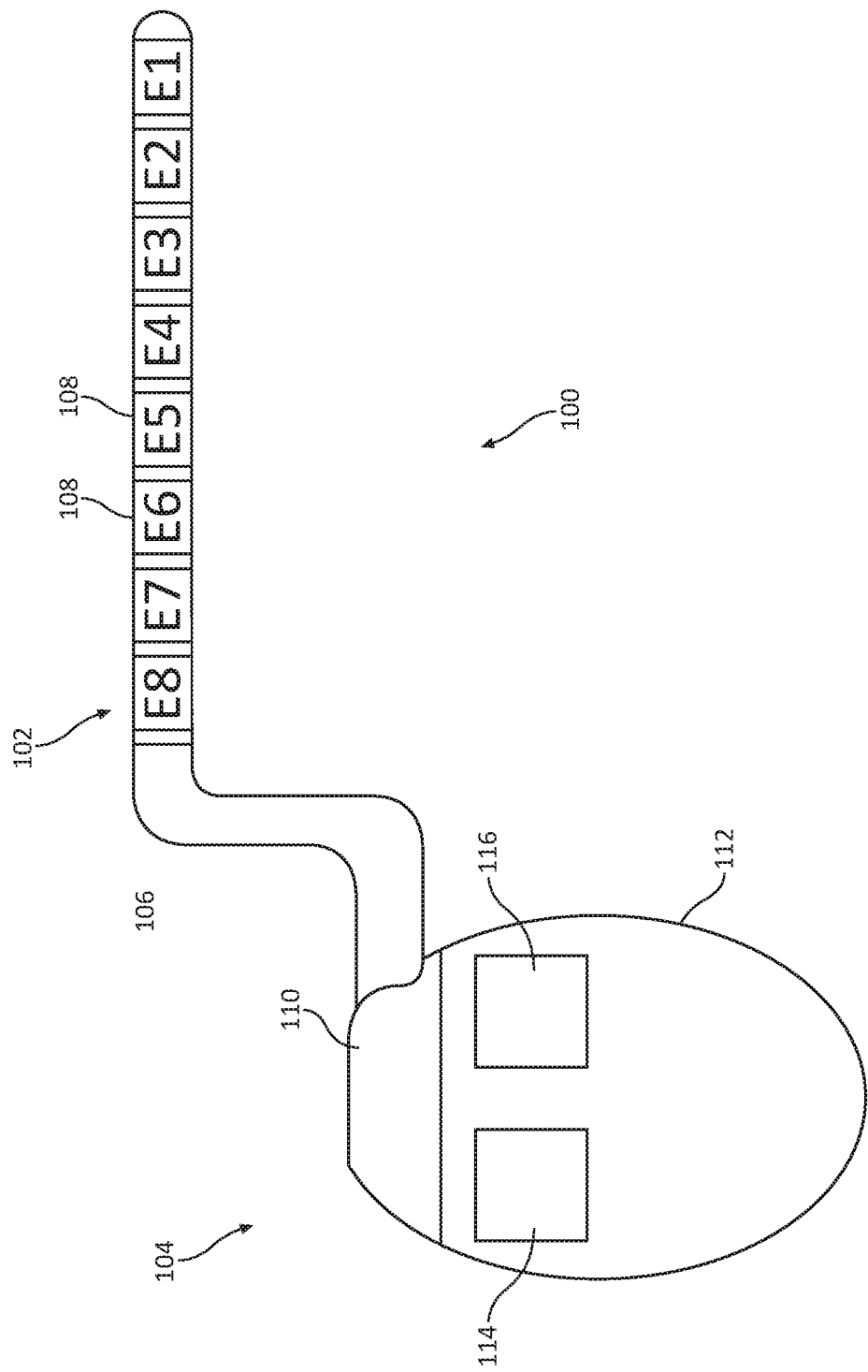
FIG. 1 is an example illustration of an adrenal gland therapy system in accordance with embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Various aspects of the present disclosure relate to apparatuses, methods, and systems directed toward neuroendocrine modulation of a patient's adrenal gland. Stimulation for depolarization of chromaffin cell membrane or splanchnic nerve effect within the adrenal medulla, for pain and non-pain symptoms of chronic fatigue syndrome and fibromyalgia and other disease states with neurotransmitter or neurohormonal dysfunction. Chromaffin cells in the adrenal medulla synthesize, store, and secret catecholamines (e.g., norepinephrine, epinephrine). Adrenal gland stimulation may lead to an increase, or produce a blocking effect in the activity of several of the catecholamine biosynthetic enzymes, and to an increase or decrease in the rate of catecholamine biosynthesis or chromaffin cell exocytosis or chromaffin cell sensitivity thereby causing secretion or blocking of catecholamines and of other chromaffin granule constituents from the chromaffin cells.

Various aspects of the present disclosure also relate to apparatuses, methods, and systems directed toward stimulation of the adrenal medulla that modulates the release of L-dopa into the systemic circulation. The stimulation in this regard may be an alternative to, or delivered in parallel with, oral pharmacologic therapy and, in embodiments, may be directed toward lessoning symptoms of degenerative neurological diseases such as Parkinson's disease. Parkinson's disease is a progressive neurodegeneration of the central nervous system, e.g., the basal ganglia, with a loss of dopamine production from dopanergic neurons within the substantia nigra of the brain or the formation of Lewy bodies (protein deposits inside of nerve cells). This results in the many motor abnormalities seen with Parkinson patients. Embodiments of the medical devices and methods discussed herein deliver stimulation to the adrenal medulla or peripheral sympathetic nerve(s) to modulate the release of L-dopa into the systemic circulation, as an alternative to, or in parallel with, oral pharmacologic therapy.

Electrical stimulation of the adrenal gland, specifically the medulla, has shown to modulate the release of dopamine in concert with norepinephrine. L-dopa is the precursor to dopamine and dopamine is the precursor for norepinephrine, all sharing the same source, tyrosine, within the medulla. L-dopa may cross the blood-brain-barrier and, thus, may facilitate keeping dopamine within a certain safety zone to mitigate blood pressure and/or gastrointestinal effects. In embodiments, the stimulation may be delivered, for example, based on individual clinical signs, with patients adjusting stimulation as needed, or based on a sensor with automatic dosing and reprogramming of the stimulation parameters based on patient needs.

FIG. 1 is an example illustration of an adrenal gland therapy system 100, which includes an adrenal gland therapy lead 102 and a controller 104 in accordance with embodiments of the disclosure. The lead 102 may include an elongated cylindrical lead body 106. The lead 102 includes a number of electrodes 108 arranged on the lead body 106. The electrodes 108 may be arranged circumferentially around the lead 102 as ring electrodes mounted around the lead body 106. In embodiments, the electrodes 108 may extend at least approximately around the circumference of the lead body 106. In embodiments, one or more of the electrodes 108 may extend partially around the circumference of the lead body 106. In some instances, for example, the plurality of electrodes 108 may be segmented electrodes that are circumferentially and axially disposed about the lead body 106. Each of the plurality of illustrated electrodes 108 is labeled E1-E8, however the actual number and shape of leads and electrodes vary according to the application.

As shown, the adrenal gland therapy lead 102 is operatively coupled to the controller 104. A connector 110 arranged with the controller 104 couples an end of the adrenal gland therapy lead 102 to the controller 104, thereby operatively (e.g., communicatively, electrically, and/or physically) coupling the electrodes 108 to the internal electronics within the controller 104. In embodiments, the controller 104 may be configured to communicate wirelessly with one or more leads 102, in which case, the controller 104 may include one or more wireless communication antennas, coils, and/or the like. The controller 104 may also include a housing 112, which contains and houses electronic and other components. In embodiments, the controller 104 may include a pulse generator that may be implantable within a patient (e.g., an implantable pulse generator (IPG)), or may be configured to be positioned external to the patient. In instances where the controller 104 is implantable, the housing 112 may be formed of an electrically conductive, biocompatible material, such as titanium, and may form a hermetically sealed compartment wherein the internal electronics are protected from the body tissue and fluids.

The housing 112 may enclose sensing circuitry 114 configured to receive, from one or more of the electrodes 108, physiological signals obtained by the one or more electrodes 108. The housing 112 may also enclose pulse generation circuitry 116 that delivers stimulation energy via one or more of the electrodes 108. According to various embodiments, the sensing circuitry 114 (or aspects thereof) and/or the pulse generation circuitry 116 (or aspects thereof) may be configured to be implanted in the patient and/or disposed external to the patient. That is, for example, in embodiments, the sensing circuitry 114 and the pulse generation circuitry 116 may be integrated within a processor disposed in an implantable medical device (e.g., the controller 104) and/or an external medical device. The sensing circuitry 114 (or aspects thereof) and/or the pulse generation circuitry 116 (or aspects thereof) may be implemented in any combination of hardware, firmware, and software. For example, the sensing circuitry 114 may be, or include, a first algorithm, virtual processor, and/or process implemented by a processor, and, similarly, the pulse generation circuitry 116 circuit may be, or include, a second algorithm, virtual processor, and/or process implemented by a processor. In embodiments, the sensing circuitry 114 may be, or include, a first set of physical and/or virtual circuit elements, and, similarly, the pulse generation circuitry 116 may be, or include, a second set of physical and/or virtual circuit elements.

In embodiments, the controller 104 may include a programmable micro-controller or microprocessor, and may include one or more programmable logic devices (PLDs) or application specific integrated circuits (ASICs). In some implementations, the controller 104 may include memory as well. Although embodiments of the present system 100 are described in conjunction with a controller 104 having a microprocessor-based architecture, it will be understood that the controller 104 (or other device) may be implemented in any logic-based integrated circuit architecture, if desired. The controller 104 may include digital-to-analog (D/A) converters, analog-to-digital (ND) converters, timers, counters, filters, switches, and/or the like.

The sensing circuitry 114 may be configured to receive a physiological signal obtained by one or more of the electrodes 108, and analyze the received physiological signal to identify a therapy region. According to embodiments, the physiological signal may include intrinsic electrical activity, a physiological response to an applied stimulation signal, and/or the like. For example, the sensing circuitry 114 may be configured to obtain a physiological signal that is a response to a stimulation signal administered using one or more of the electrodes 108, and to analyze that signal to identify a therapy location. In embodiments, the sensing circuitry 114 may be configured to evaluate motion of the patient, electrical activity of the adrenal gland, and/or other physiological signals to identify a therapy region.

The therapy region may be, in embodiments, a region including a portion of an adrenal gland that is identified as being likely to be associated with an adrenal gland condition. For example, in implementations used for treating disorders such as chronic fatigue syndrome, fibromyalgia, orthostatic intolerance, irritable bowel syndrome (IBS), Crohn's disease, mood disorders/depression, or other disease states with neurotransmitter or neurohormonal dysfunction, a clinician may insert the adrenal gland therapy lead 102 near or on a region of one or both of the patient's adrenal glands associated with the disorder, operate the controller 104 (e.g., manually, if the controller 104 is external, and via telemetry if the controller 104 is implanted), causing the controller 104 to deliver stimulation energy to a selected region via one or more of the electrodes 108. By evaluating an electrical response obtained by one or more of the electrodes 108, the controller 104 and/or the clinician may determine whether the selected region is a therapy region (e.g., the selected region may be identified as a therapy region if the physiological response to the stimulation indicates a therapeutic effect). In embodiments, the clinician may identify a therapy region by determining a region of the adrenal gland(s) for which administering stimulation energy results in at least some improvement in symptoms.

The stimulation energy may be in the form of a pulsed electrical waveform to one or more of the electrodes 108 in accordance with a set of stimulation parameters, which may be programmed into the controller 104, transmitted to the controller 104, and/or the like. Stimulation parameters may include, for example, electrode combinations that define the electrodes that are activated as anodes (positive), cathodes (negative), turned on, turned off (zero), percentage of stimulation energy assigned to each electrode (fractionalized electrode configurations), and/or electrical pulse parameters, which define the pulse amplitude (measured in milliamps or volts depending on whether the controller 104 supplies constant current or constant voltage to one or more of the electrodes 108), pulse duration (measured in microseconds), pulse rate (measured in pulses per second), pulse waveform, and/or burst rate (measured as the stimulation on duration X and stimulation off duration Y). The pulse generation circuitry 116 may be capable of delivering the stimulation energy to the one or more of the electrodes 108 over multiple channels or over only a single channel. Stimulation energy may be used to identify therapy regions and/or to provide stimulation therapy to identified therapy regions or alter therapy regions over time to prevent exhaustion in one location.

Stimulation energy may be transmitted to the tissue in a monopolar (or unipolar) or multipolar (e.g., bipolar, tripolar, etc.) fashion. Monopolar stimulation occurs when a selected one or more of the electrodes 108 is activated and transmits stimulation energy to tissue. Bipolar stimulation, a type of multipolar stimulation, occurs when two of the electrodes 108 are activated as anode and cathode, so that stimulation energy is transmitted between the activated electrodes. Multipolar stimulation also may occur when more than two (e.g., three, four, etc.) of the electrodes 108 are activated, e.g., two as anodes and a third as a cathode, or two as cathodes and a third as an anode. In certain instances, the pulse generation circuitry 116 may individually control the magnitude of electrical current flowing through each of the electrodes. In these instances, current generators may be used to supply current-regulated amplitudes to selectively generate independent current sources for one or more of the electrodes 108.

Figure 2:
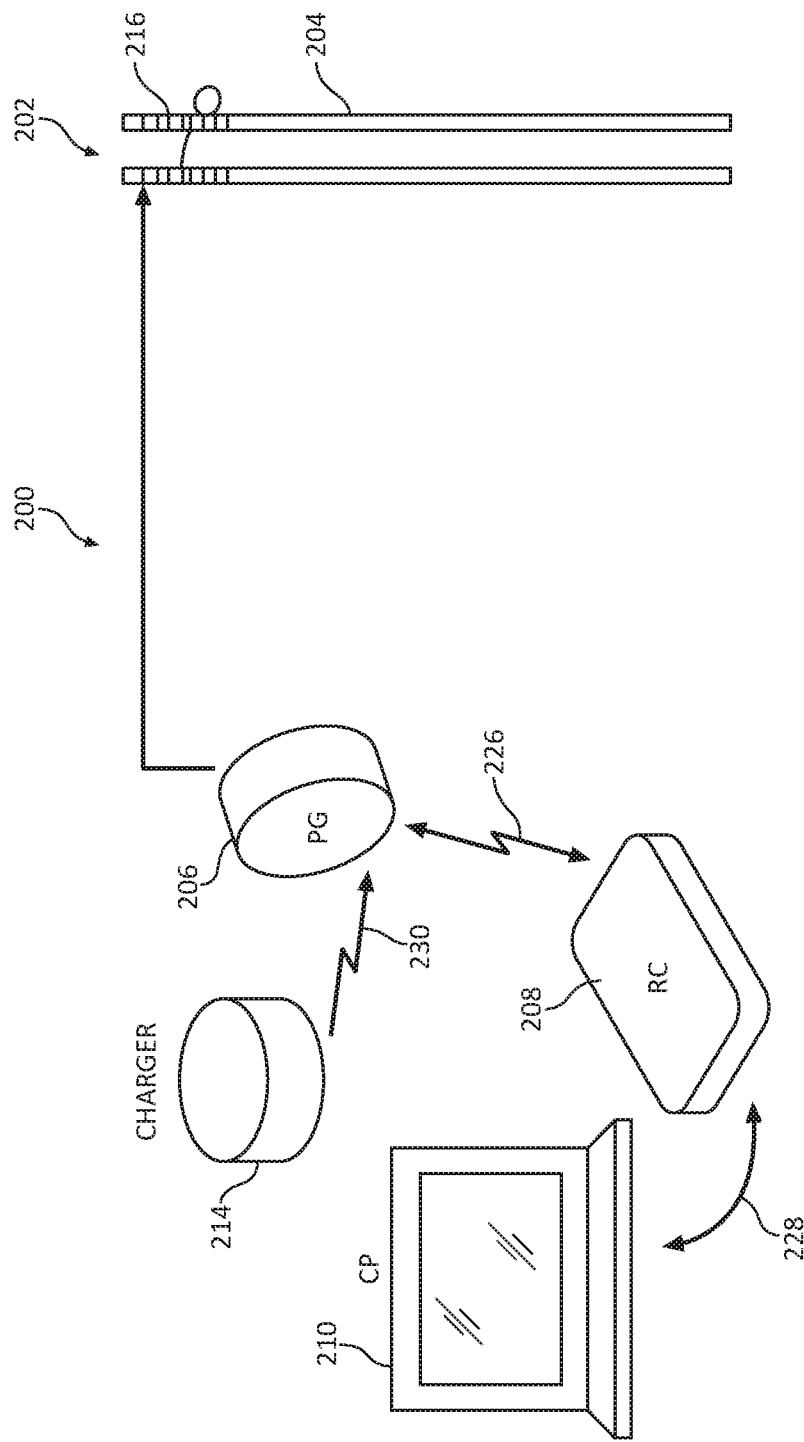
FIG. 2 is a plan view of an adrenal gland therapy system in accordance with embodiments of the disclosure.

FIG. 2 is a plan view of an adrenal gland therapy system 200 in accordance with embodiments of the disclosure. The adrenal gland therapy system 200 may include at least one implantable adrenal gland stimulation lead 202, 204, a pulse generator (PG) 206, an external remote controller (RC) 208, a clinician's programmer (CP) 210, and an external charger 214. In certain instances, the PG 206 may be operatively coupled (and, in embodiments, physically coupled) to one or both of the adrenal gland stimulation leads 202, 204, which may carry a number of electrodes 216 arranged in an array. The PG 206 may include pulse generation circuitry that delivers electrical stimulation energy in the form of a pulsed electrical waveform (i.e., a temporal series of electrical pulses) to the plurality of electrodes 216 in accordance with a set of stimulation parameters. The PG 206 may be an implantable PG (and IPG), an external PG, or may represent an operatively coupled system including one or more implantable devices and/or one or more external devices.

In certain instances, the RC 208 may be used to telemetrically control the PG 206 via a communications link 226. The RC 208 may also modify programmed stimulation parameters to actively control the characteristics of the electrical stimulation energy output by the PG 206. The RC 208 may perform these functions by indirectly communicating with the PG 206 through the RC 208, via a communications link 226. Alterations to the stimulation parameters or stimulation characteristics may be altered using the CP 210. The CP 210 may directly communicate with the PG 206 and via a communications link. The external charger 214 may be a portable device used to charge the PG 206 via a charging link 230, which may be, e.g., an inductive charging link, a radio frequency (RF) charging link, illumination, ultrasound, magnetics, and/or the like.

In embodiments, of the communication links 226, 228, and 230 may be, or include, a wireless communication link such as, for example, a short-range radio link, such as Bluetooth, IEEE 802.11, a proprietary wireless protocol, and/or the like. In embodiments, for example, one or more of the communication links 226, 228, and 230 may utilize Bluetooth Low Energy radio (Bluetooth 4.1), or a similar protocol, and may utilize an operating frequency in the range of 2.40 to 2.48 GHz. The term "communication link" may refer to an ability to communicate some type of information in at least one direction between at least two devices, and should not be understood to be limited to a direct, persistent, or otherwise limited communication channel. That is, according to embodiments, a communication link may be a persistent communication link, an intermittent communication link, an ad-hoc communication link, and/or the like. A communication link may refer to direct communications between one or more devices, and/or indirect communications that travel between the one or more devices via at least one other device (e.g., a repeater, router, hub, and/or the like). A communication link may facilitate uni-directional and/or bi-directional communication between the linked devices.

Any number of a variety of communication methods and protocols may be used, via communication links, to facilitate communication between devices in the adrenal gland therapy system 200. For example, wired and/or wireless communications methods may be used. Wired communication methods may include, for example and without limitation, traditional copper-line communications such as DSL, broadband technologies such as ISDN and cable modems, and fiber optics, while wireless communications may include cellular communications, satellite communications, radio frequency (RF) communications, infrared communications, induction, conduction, acoustic communications, and/or the like.

The illustrative components shown in FIGS. 1 and 2 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 1-2 may be, in embodiments, integrated with various other components depicted therein (and/or components not illustrated), all of which are considered to be within the ambit of the disclosed subject matter. For example, the adrenal gland stimulation leads described with reference to FIG. 1, 3, or 4 may be used in the adrenal gland therapy system 200. Further, the adrenal gland therapy system 200 may form a portion of the system described with reference to FIG. 6.

Figure 3A:
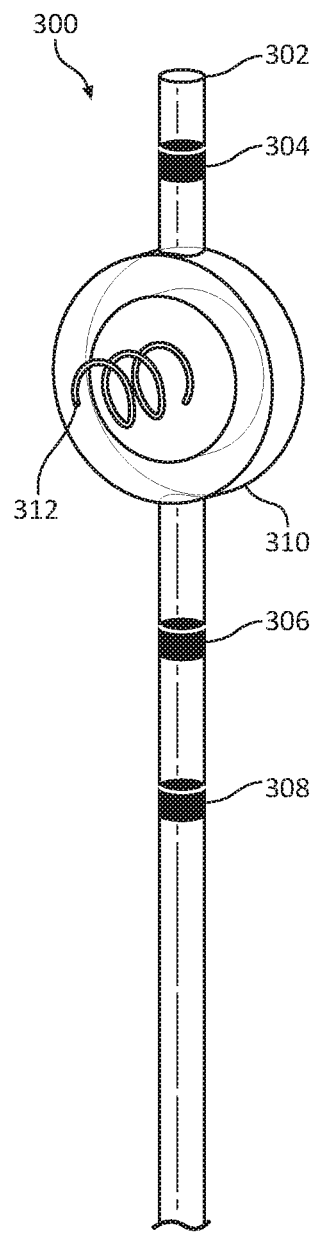
FIG. 3A is an example illustration of an adrenal gland therapy lead configuration in accordance with embodiments of the disclosure.
Figure 3B:
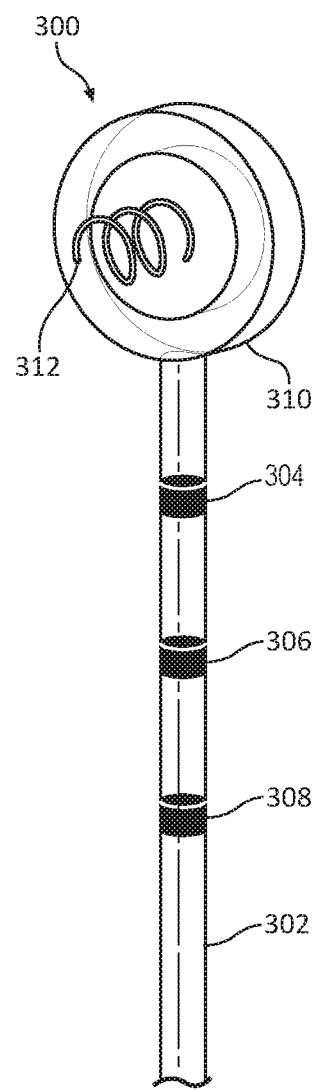
FIG. 3B is an example illustration of another adrenal gland therapy lead configuration in accordance with embodiments of the disclosure.
Figure 3C:
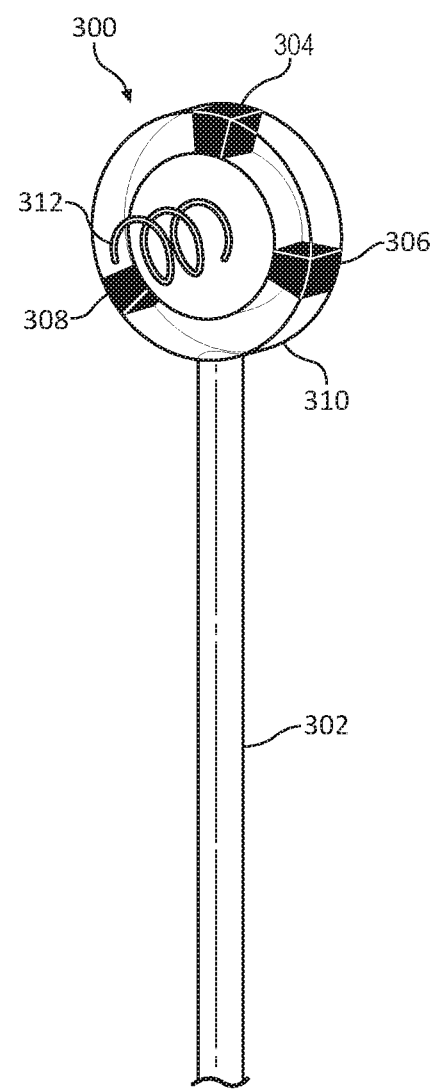
FIG. 3C is an example illustration of another adrenal gland therapy lead configuration in accordance with embodiments of the disclosure.

FIGS. 3A-C are example illustrations of an adrenal gland therapy lead 300 having different configurations in accordance with embodiments of the disclosure. The adrenal gland therapy lead 300 may be used alone for delivering therapy to an adrenal gland of a patient or as part of apparatuses, methods, or systems for delivering therapy to an adrenal gland of a patient. The adrenal gland therapy lead 300 may include a lead body 302 and a plurality of electrodes 304, 306, 308 arranged therewith. The adrenal gland therapy lead 300 may be connected with a controller (e.g., as shown and descried with reference to FIGS. 1 and 2) to supply stimulation parameters to the plurality of electrodes 304, 306, 308 arranged along the lead body 302. The lead body 302 may be configured to attach to a portion of the adrenal gland of the patient and engage a capsule of the adrenal gland. The lead body 302 may be configured to attach to a portion of the adrenal gland of the patient and engage the renal fascia, Gerota's fascia, the perirenal fat, the periphrenic space, the anterior pararenal space, capsule or cortex. In addition and as described in further detail with reference to, for example, FIGS. 5-6, at least one of the plurality of electrodes 304, 306, 308 is configured to deliver stimulation energy to modulate catecholamine release from chromaffin cells within the adrenal gland. The adrenal gland therapy lead 300 may also include a button 310 configured to facilitate attachment of the lead to the adrenal gland, and stimulation thereof, and a helical anchor 312. In addition, one or more of the plurality of electrodes 304, 306, 308 may be configured to sense the catecholamines released as a result of the delivered stimulation energy. The button 310 may be formed of a material having the same properties as the lead body 302. In certain instances, the button 310 may be sized and shaped to provide a larger surface area of stimulation, compared to the lead body 302, by arranging the plurality of electrodes 304, 306, 308 thereon.

The button 310 may have a flexibility greater than the lead body 302, and may be configured to conform to the adrenal gland for attachment thereto. More specifically, the button 310 may take the shape of the adrenal gland upon attachment thereto. In addition, the button 310 may have a width less than a width of the lead body 302. In certain instances, the button 310 may be the portion of the adrenal gland therapy lead 300 that attaches to a portion of the adrenal gland. The adrenal glands are surrounded by a fatty capsule. The button 310 may be attached to an exterior surface of the capsule, within the capsule, an interior surface of the capsule (e.g., between the capsule and the adrenal gland), or directly to the adrenal gland. Thus, the width of the button 310 may be approximately equal to or less than the capsule of the adrenal gland.

The helical anchor 312 may be configured to anchor to the lead body 302 directly or indirectly (via the capsule) to the adrenal gland. In certain instances, the helical anchor 312 may be configured as an electrode in addition to the electrodes 304, 306, 308. A length of the helical anchor 312 may be dependent on the anchoring location (e.g., a longer length when anchoring to the adrenal gland as compared to anchoring to the capsule or adrenal gland parenchyma). The helical anchor 312 may be configured to mitigate against migration of the lead body 302 when implanted, and ensure positive fixation on the adrenal gland.

In addition, the button 310 may be arranged along any portion of the lead body 302. As shown in FIG. 3A, the button 310 is arranged along an intermediate portion of the lead body 302. The lead body 302 includes some of the plurality of electrodes 304, 306, 308 on one side of the button 310, and others of the plurality of electrodes 304, 306, 308 on the other side of the button 310. In certain instances, the position of the button 310 may be adjusted after implantation and/or fixation of the button 310 to the adrenal gland. The button 310 may frictionally engage the lead body 302 such that a force applied by a physician would overcome the coupling of the button 310 to the lead body 302. The button 310 may also be attached or couple to the lead body 302 by a medical adhesive. A physician may adjust the positioning of the button 310 prior to implantation of the lead body 302, or after fixation of the button 310 to the adrenal gland. As a result, the physician may adjust the positioning of the plurality of electrodes 304, 306, 308 relative to the adrenal gland by shifting the button 310 along a length of the lead body 302 prior to or after implantation and/or fixation of the button 310 to the adrenal gland. As shown in FIG. 3B, the button 310 may be coupled or attached to a distal end of the lead body 302. In certain instances, the distal end of the lead body 302 may include multiple buttons 310.

As shown in FIG. 3C, the plurality of electrodes 304, 306, 308 may be arranged around a perimeter of the button 310. In certain instances, arranging the plurality of electrodes 304, 306, 308 in this manner may facilitate directing stimulation energy to a smaller target area as opposed to across a length of the lead body 302.

Figure 4A:
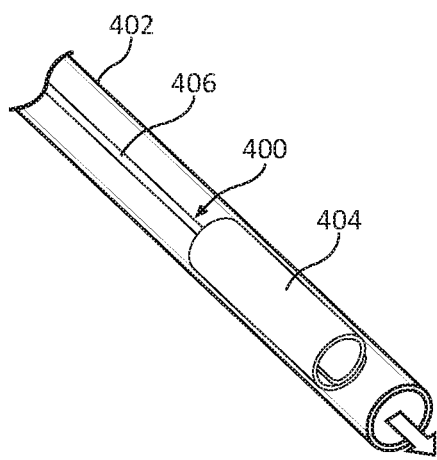
FIG. 4A is an example illustration of an adrenal gland therapy lead and deployment system in accordance with embodiments of the disclosure.

FIG. 4A is an example illustration of an adrenal gland therapy lead 400 and deployment system 402 in accordance with embodiments of the disclosure. As shown in FIG. 4A, the adrenal gland therapy lead 400 is arranged within the deployment system 402. The adrenal gland therapy lead 400 may be used alone for delivering therapy to an adrenal gland of a patient or as part of apparatuses, methods, or systems for delivering therapy to an adrenal gland of a patient. The adrenal gland therapy lead 400 may include a paddle component 404. The deployment system 402 may have a cylindrical shape with a circular opening at a distal end thereof. The adrenal gland therapy lead 400, including a lead body 406, may be loaded into the delivery system 402 at either end. In the loading the adrenal gland therapy lead 400 therein, the paddle component 404 may collapse within the deployment system 402. As shown in FIG. 4A, the paddle component 404 may roll upon itself to collapse within the deployment system 402. In certain instances, the paddle component 404 may fold, crease, pleat, or bend to collapse within the deployment system 402. In certain instances, the deployment system 402 may be a delivery catheter.

Figure 4B:
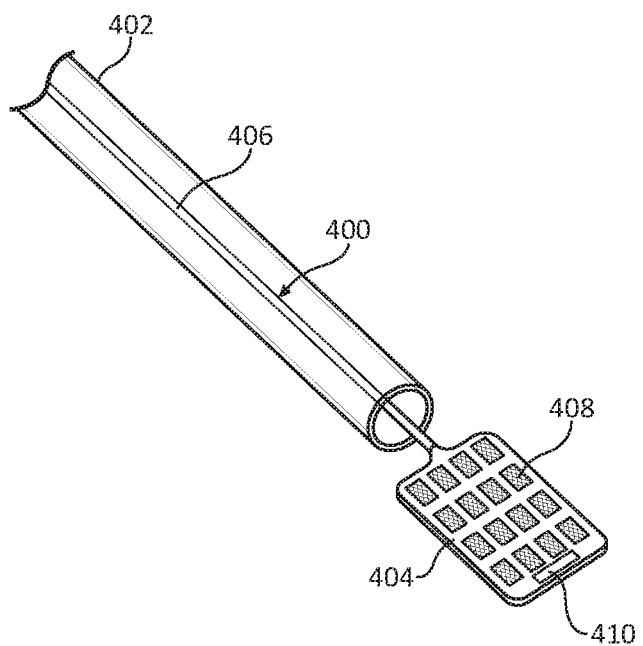
FIG. 4B is an example illustration of the adrenal gland therapy lead shown in FIG. 4B, deployed from the deployment system in accordance with embodiments of the disclosure.

FIG. 4B is an example illustration of the adrenal gland therapy lead 400 shown in FIG. 4B, deployed from the deployment system 402 in accordance with embodiments of the disclosure. FIG. 4B shows the adrenal gland therapy lead 400 in a deployed/delivered configuration, whereas FIG. 4A shows the adrenal gland therapy lead 400 in a delivery configuration. The paddle component 404 may be configured to expand to the deployed configuration, shown in FIG. 4B, in response to deployment from the deployment system 402, and fold and collapse to the delivery configuration, shown in FIG. 4A, in response to retraction within the deployment system 402.

In addition and as shown in FIG. 4, the paddle component 404 may include a plurality of electrodes 408. The plurality of electrodes 408 are arranged on a paddle component 404, which may be arranged at a distal end of the lead body 406. The plurality of electrodes 408 may be configured to deliver stimulation energy therethrough to modulate catecholamine release from chromaffin cells within at the adrenal glands of the patient. The adrenal gland therapy lead 400 may be connected with a controller (e.g., as shown and descried with reference to FIGS. 1 and 2) to supply stimulation parameters to the plurality of electrodes 408 arranged with the paddle component 404. In addition, one or more of the plurality of electrodes 408 may be configured to sense a biomarker affected by the delivered stimulation energy. The sensed level of catecholamines released may be provided as feedback to the controller, which may alter the stimulation energy to achieve a desired catecholamine release level. In certain instances, the paddle component 404 may include a thermoelectric element 410 arranged therewith. The thermoelectric element 410 may provide a cooling effect to the adrenal gland. As described in further detail with reference to FIGS. 7A-B, the thermoelectric element 410 cooling the adrenal gland may also modulate catecholamine release from chromaffin cells within the adrenal gland. More specifically, the thermoelectric element 410 (e.g., a Peltier element) may be configured to cool the periglandular region of the adrenal gland. Applying the thermoelectric element 410 to the medulla (in, on or near) may a resultant effect of modulating the circulating levels of catecholamines within the bloodstream. In certain instances, the thermoelectric element 410 may apply a cooling effect within the intravascular space at, within or near the arterial supply to the adrenal gland. The thermoelectric element 410 may supply a cooling at a temperature range from 4 degrees Celsius to 32 degrees Celsius.

In certain instances, the lead body 406, or a portion thereof, may be configured to attach to a portion of an adrenal gland of the patient. More specifically, the paddle component 404 or the lead body 406 may be configured to engage a capsule of one of the adrenal glands. As noted above, the paddle component 404 may be flexible and configured to engage and attach to the portion (e.g., the capsule) of the adrenal gland of the patient in the delivery configuration. The paddle component 404 may at least partially conform to the adrenal gland, and mitigate against resistant of the adrenal gland therapy lead 400. In certain instances, the paddle component 404 may be implanted between the capsule and the adrenal gland, which may further mitigate against resistant of the adrenal gland therapy lead 400. In other instances, the lead body 406 and/or the paddle component 404 may also include a barb(s), a rigid helix(s) and/or a talon(s) (not shown) for mechanical attachment to the adrenal gland. The lead body 406 may also include a suture feature (e.g., a suture hole, through which a suture may be arranged) to secure the lead body 406 in place. In other instances, in addition to or in place of the mechanical attachment mechanisms, tissue glue, an adhesive, and/or a hydrogel or hydrogel/polymer type may be applied to the lead body 406 and/or the paddle component 404 for adhesive attachment of the lead body 406 and/or the paddle component 404 to the adrenal gland.

Figure 4C:
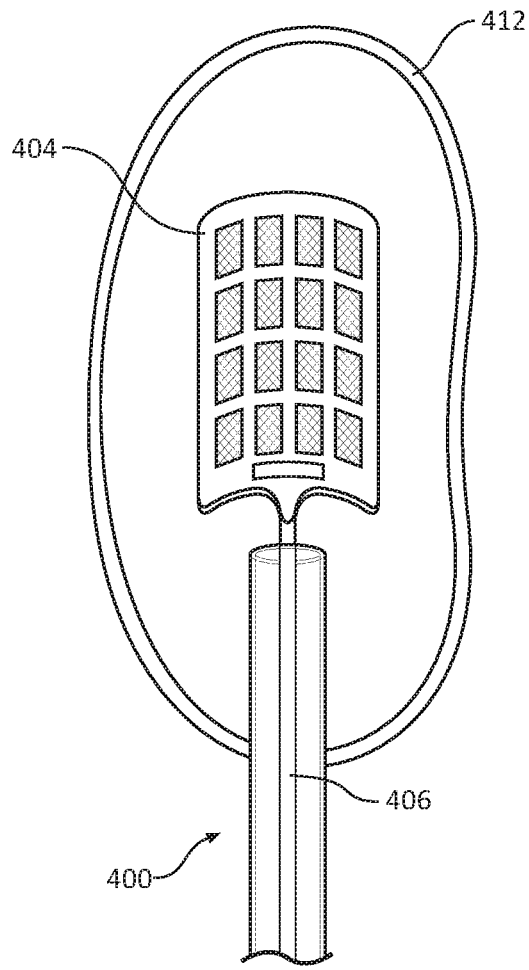
FIG. 4C is an example illustration of the adrenal gland therapy lead shown in FIGS. 4A-B, deployed on an adrenal gland in accordance with embodiments of the disclosure.

FIG. 4C is an example illustration of the adrenal gland therapy lead 400 shown in FIGS. 4A-B, deployed on an adrenal gland 412 in accordance with embodiments of the disclosure. As shown in FIG. 4C, the paddle component 404 flexes and is configured to engage and attach to a portion of the adrenal gland 412. A physician placing the adrenal gland therapy lead 400 may fluoroscopically visualize the orientation of the plurality of electrodes 408. In other instances, one or both of the lead body 406 and the paddle component 404 may include radiopaque markers (not shown) to assist in visualizing the adrenal gland therapy lead 400. In certain instances, the paddle component 404 may be a wrap or mesh.

Figure 4D:
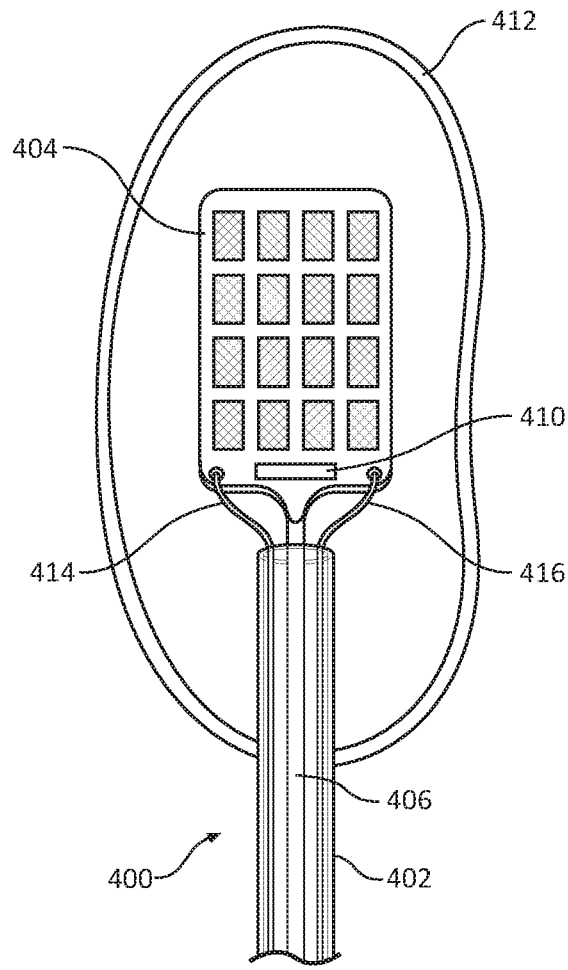
FIG. 4D is an example illustration of the adrenal gland therapy lead shown in FIGS. 4A-C, including tethers in accordance with embodiments of the disclosure.

FIG. 4D is an example illustration of the adrenal gland therapy lead 400 shown in FIGS. 4A-C, including tethers 414, 416 in accordance with embodiments of the disclosure. The tethers 414, 416 may be attached to the paddle component 404, and assist in repositioning of the paddle component 404 relative to the adrenal gland 412. The tethers 414, 416 may extend from the paddle component 404 and along the lead body 406. The tethers 414, 416 may extend along an entire length of the lead body 406, in certain instances, such that a physician or user may manipulate the tethers 414, 416. In other instances, the tethers 414, 416 may be attached to a portion of the lead body 406 such that manipulation of the lead body 406 indirectly manipulates the tethers 414, 416 and the paddle component 404. Tensioning the tethers 414, 416 may withdraw the paddle component 404 within the deployment system 402. As a result, tensioning the tethers 414, 416 may allow for repositioning of the paddle component 404 after deployment from the deployment system 402 or removal of the adrenal gland therapy lead 400 entirely. More specifically, the paddle component 404 may be reconfigured to the delivery configuration, as shown in FIG. 4A, and redeployed if the positioning of the paddle component 404 as desired or removed from the adrenal gland 412 along with the deployment system 402.

Figure 5:
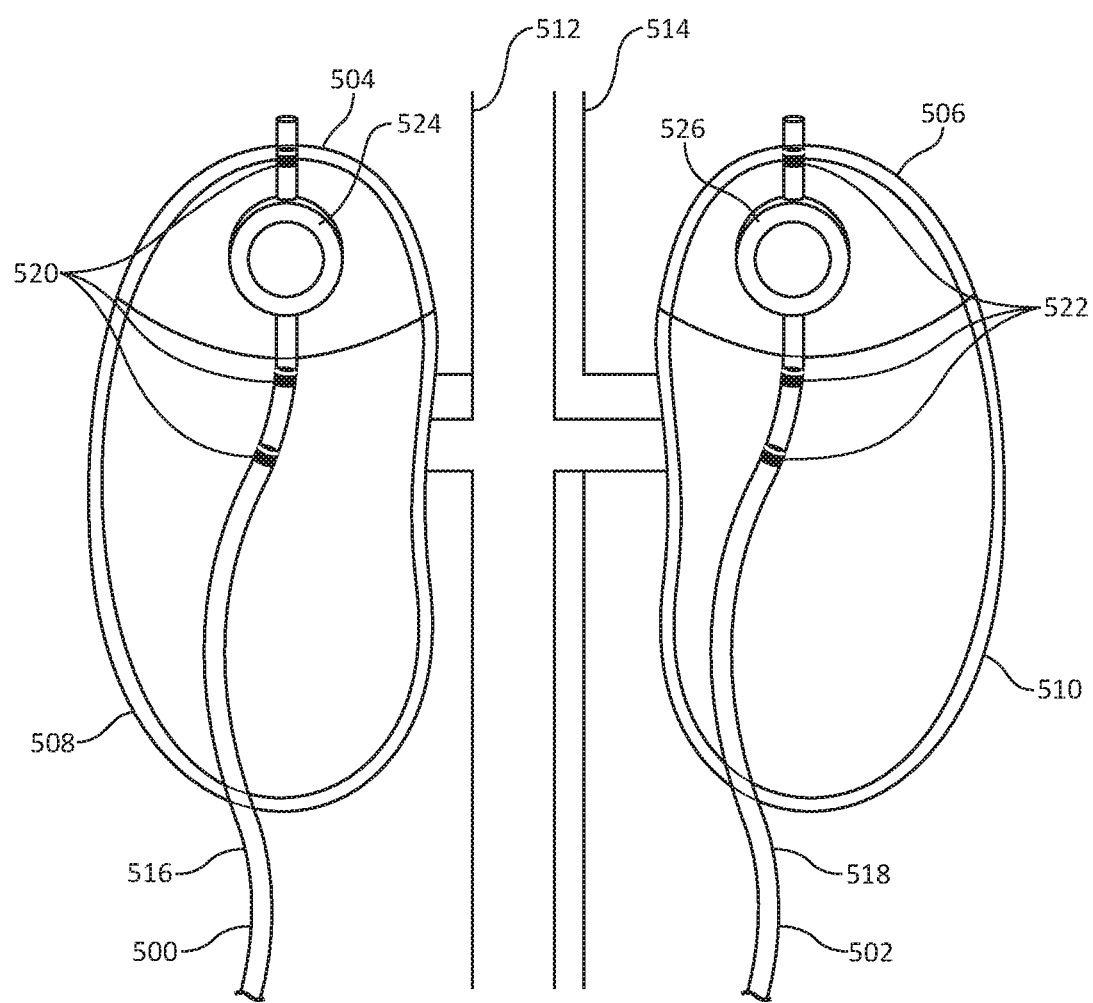
FIG. 5 is an example illustration of adrenal gland therapy leads in accordance with embodiments of the disclosure.

FIG. 5 is an example illustration of adrenal gland therapy leads 500, 502 in accordance with embodiments of the disclosure. The adrenal gland therapy leads 500, 502 are shown arranged on adrenal glands 504, 506 of a patient. The adrenal glands 504, 506 are located above the patient's kidneys 508, 510, which are located on either side of the patient's vena cava 512 and aorta 514. The adrenal gland therapy leads 500, 502 may be delivered and attached, directly or indirectly to the adrenal glands 504, 506 (or Gerota's fascia) by a laparoscopic procedure, open laparotomy procedure, or other minimally invasive procedure.

Each of adrenal gland therapy leads 500, 502 may have a lead body 516, 518 and a set of a plurality of electrodes 520, 522 arranged therewith. The plurality of electrode sets 520, 522 may be arranged longitudinally along the adrenal glands 504, 506. In certain instances, distal portions of each lead body 516, 518 (e.g., portions having the plurality of electrode sets 520, 522) may have a greater flexibility (e.g., more pliable polyurethane) than other portions of the lead body 516, 518 or the distal portions of each lead body 516, 518 may be formed from other materials (Pebax®, polyethylene, or Hytrel®) (polyester)). The added flexibility of the lead body 516, 518 or portions of the lead body 516, 518 may assist in mitigate against movement of the adrenal gland therapy leads 500, 502 when attached to the adrenal glands 504, 506. The added flexibility of portions of the lead body 516, 518 may act as a strain relief mechanism such that movement in other portions imparted on other portions of the lead body 516, 518 is isolated and/or indirectly absorbed. In other instances, the lead body 516, 518 of each of the adrenal gland therapy leads 500, 502 may be attached to the adrenal glands 504, 506 with additional length or slack, between the adrenal glands 504, 506 and implant location of a controller coupled to each lead body 516, 518, to provide additional flexibility for the absorption of the patient's movement.

Each lead body 516, 518 may also include a button 524, 526. The button 524, 526 of each lead body 516, 518 may have a flexibility greater than each lead body 516, 518, and may be configured to conform to the adrenal glands 504, 506 for attachment thereto. More specifically, each button 524, 526 may take the shape of the adrenal glands 504, 506. The adrenal glands 504, 506 are surrounded by a fatty capsule (as shown in further detail in FIG. 6). Each button 524, 526 may be attached to an exterior surface of the capsule, within the capsule, an interior surface of the capsule (e.g., between the capsule and the adrenal gland), or directly to the adrenal glands 504, 506.

In certain instance, each lead body 516, 518 and/or each button 524, 526 may include a barb(s), a rigid helix(s), and/or a talon(s) for mechanical attachment (not shown) to the adrenal glands 504, 506. In other instances, in addition to or in place of the mechanical attachment mechanisms, tissue glue, an adhesive, and/or a hydrogel may be applied to each lead body 516, 518 and/or each button 524, 526 for attachment to the adrenal glands 504, 506.

As noted above, the adrenal gland therapy leads 500, 502 may be connected with a controller (e.g., as shown and descried with reference to FIGS. 1 and 2). The controller may be configured to instruct delivery of the stimulation energy through one or more of the electrodes in the plurality of electrode sets 520, 522 to modulate catecholamine release from chromaffin cells within at least one of the adrenal glands 504, 506. In certain instances, the controller may be configured to intermittently or continuously instruct delivery of the stimulation energy through different combinations of the one or more of the electrodes in the plurality of electrode sets 520, 522. More specifically, the controller (not shown) may include circuitry (e.g., as described with reference to FIG. 1) that instructs delivery of the stimulation energy through one or more of the electrodes the plurality of electrode sets 520, 522 on a duty cycle based on a metabolization time of catecholamine or clinical signs of the patient. The duty cycle may include applying stimulation for 25% of a time period (e.g., minutes, hour or day), and withhold stimulation for 75% the time period (e.g., minutes, hour or day). Continuous stimulation through one or more of the adrenal glands 504, 506 may not be necessarily required for reaching therapeutic levels of catecholamine. The duty cycle control of delivery of the stimulation energy may reduce battery consumption and reduces chances of attenuated effectiveness over time due to adaptation or depletion of the adrenal glands 504, 506. In addition, the stimulation energy may be delivered at a frequency between 2 Hz and 20 kHz (e.g., 2 Hz-50 Hz, 50 Hz-100 Hz, 100 Hz-500 Hz, 500 Hz-1 kHz, 1 kHz-5 kHz, 5 kHz-10 kHz, 10 kHz-20 kHz or any combination thereof). The stimulation energy may be applied as bursts of energy include pulses at a frequency between 2 Hz and 20 kHz or continuously. In addition, the frequency and/or pulse width stimulation energy may also be altered continuously or periodically altered over time. Altering the current, frequency and/or pulse width may reduce the chances of attenuated effectiveness of the stimulation over time due to adaptation of the adrenal glands 504, 506. In any of these instances, the stimulation energy delivered may be altered in response to patient feedback based on the physical symptoms of the patient.

In addition, stimulation energy may be transmitted to the adrenal glands 504, 506 in a monopolar or multipolar (e.g., bipolar, tripolar, etc.) fashion. Monopolar stimulation occurs when a selected one or more of the electrodes the plurality of electrode sets 520, 522 is activated and transmits stimulation energy to tissue. Bipolar stimulation, a type of multipolar stimulation, occurs when two of the electrodes in the plurality of electrode sets 520, 522 are activated as anode and cathode, so that stimulation energy is transmitted between the activated electrodes. Multipolar stimulation also may occur when more than two (e.g., three, four, etc.) of the electrodes in the plurality of electrode sets 520, 522 are activated, e.g., two as anodes and a third as a cathode, or two as cathodes and a third as an anode. In addition, the stimulation energy may be fractionalized across one or more of the electrodes in the plurality of electrode 520 and separately fractionalized across one or more of the electrodes in the plurality of electrode 522.

In certain instances, the controller may instruct delivery of the stimulation energy to one of the adrenal glands 504, 506 at a time. In addition, the controller may test between the electrode sets 520, 522 to determine which of the electrode sets 520, 522 achieves a desired response (e.g., based on patient feedback and or measuring the levels of catecholamine in the patient). More specifically and in certain instances, one of the adrenal glands 504, 506 may respond to the stimulation differently than the other one of the adrenal glands 504, 506. Thus, the controller may alter delivery of the stimulation to target one or both of the adrenal glands 504, 506 to achieve a desired response in response to measurement of a physiological sensor and/or input from the patient. The simulation energy may be delivered to one or both of the electrode sets 520, 522 to coordinate stimulation of the adrenal glands 504, 506. Both adrenal glands 504, 506 may be stimulated at the same time, or the stimulation applied thereto could be staggered (e.g., according to a duty cycle as noted above). In certain instances, the coordinated stimulation of the adrenal glands 504, 506 may reduce chances of attenuated effectiveness over time due to adaptation/tolerance of the adrenal glands 504, 506. The sensed level of catecholamines released may be provided as feedback to the controller, which may alter the stimulation energy to achieve a desired catecholamine release level.

The illustrative components shown in FIG. 5 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 1-4 may be, in embodiments, integrated with various other components depicted therein (and/or components not illustrated), all of which are considered to be within the ambit of the disclosed subject matter. For example, the adrenal gland stimulation leads 500, 502 may be used in connection with the systems described with reference to FIG. 1 and FIG. 2. In addition, the adrenal gland stimulation leads 500, 502 may include the helical anchors 312 as shown in FIG. 3, or the thermoelectric element 410 or the paddle component 404 as shown in FIG. 4.

Figure 6:
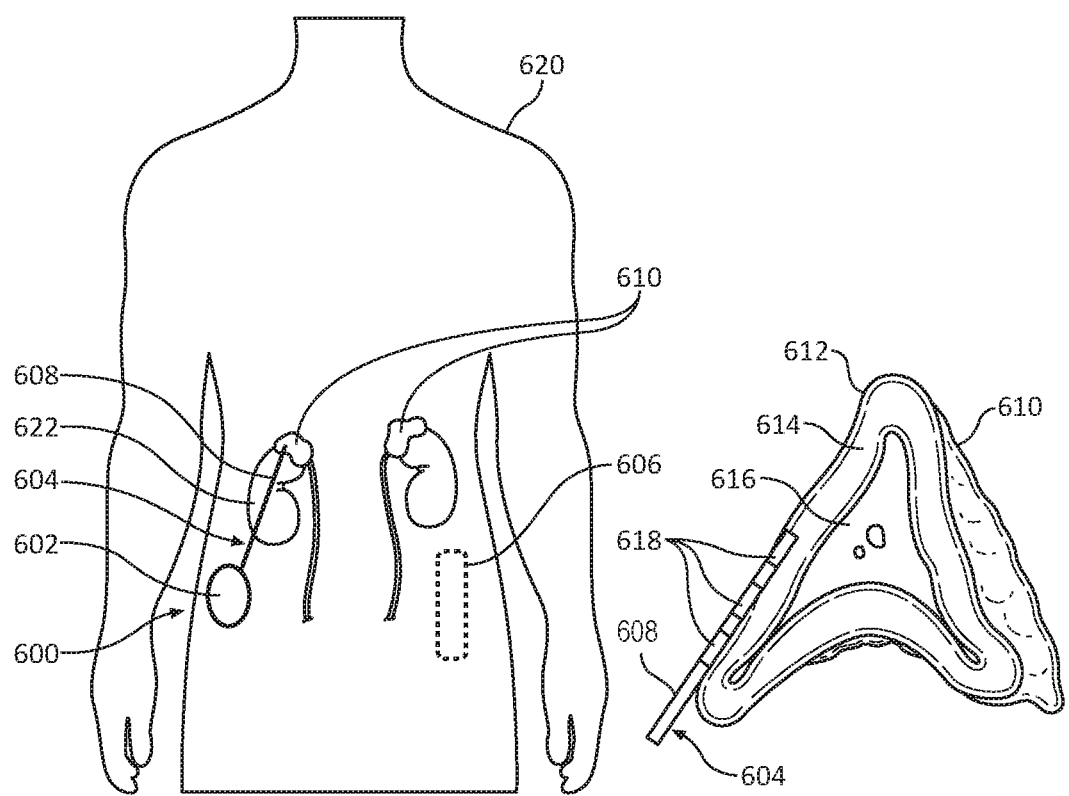
FIG. 6 is an example illustration of an adrenal gland therapy system in accordance with embodiments of the disclosure.

FIG. 6 is an example illustration of an adrenal gland therapy system 600 in accordance with embodiments of the disclosure. The adrenal gland therapy system 600 includes a controller 602 (e.g., a pulse generator) that houses electronic and other components, an adrenal gland stimulation lead 604 coupled to the controller 602, and optionally a physiological sensor 606. The adrenal gland stimulation lead 604 may include a lead body 608 that is configured engage an adrenal gland 610 of a patient 620. More specifically, the lead body 608 may configured to engage a capsule 612 of the adrenal gland 610. FIG. 6 also includes an inset portion highlighting the anatomy of the adrenal gland 610. The capsule 612 surrounds the adrenal gland 610, located above the kidney 622. The lead body 608 may be attached to an exterior surface of the capsule 612, within the capsule 612, an interior surface of the capsule 612 (e.g., between the capsule and the remaining portions of the adrenal gland 610). The adrenal gland 610 also includes a cortex 614 which produces steroid hormones and a medulla 616. Chromaffin cells in the medulla 616 synthesize, store, and secret catecholamines (e.g., norepinephrine, dopamine). The lead body 608 may also attach to the cortex 614 or medulla 616 (by way of a mechanical attachment mechanism as described, for example, with reference to FIGS. 3A-C or adhesive attachment mechanism).

The lead body 608 also includes a plurality of electrodes 618 arranged along the lead body 608. The plurality of electrodes 618 may be configured to deliver stimulation energy through at least one of the plurality of electrodes 618 to modulate catecholamine release from chromaffin cells within the adrenal gland 610. The controller 602, physically connected to the lead body 608 and electronically coupled to the plurality of electrodes 618, may be configured to instruct delivery of the stimulation energy through one or more of the plurality of electrodes 618 to modulate catecholamine release from chromaffin cells. Stimulation energy may be transmitted to the adrenal gland 610 in a monopolar or multipolar (e.g., bipolar, tripolar, etc.) fashion. Monopolar stimulation occurs when a selected one or more of the electrodes the plurality of electrodes 618 is activated and transmits stimulation energy to tissue. Bipolar stimulation, a type of multipolar stimulation, occurs when two of the electrodes in the plurality of electrodes 618 are activated as anode and cathode, so that stimulation energy is transmitted between the activated electrodes. Multipolar stimulation also may occur when more than two (e.g., three, four, etc.) of the electrodes in the plurality of electrode sets 618 are activated, e.g., two as anodes and a third as a cathode, or two as cathodes and a third as an anode. In addition, the stimulation energy may be fractionalized across one or more of the electrodes in the plurality of electrodes 618. The level of catecholamines released may be sensed by the physiological sensor 606 and provided as feedback to the controller 602, which may alter the stimulation energy to achieve a desired catecholamine release level.

In certain instances, the controller may be configured to intermittently or continuously instruct delivery of the stimulation energy through different combinations of the one or more of the plurality of electrodes 618. In addition, the controller 602 may include circuitry (e.g., as described with reference to FIG. 1) that instructs delivery of the stimulation energy through one or more of the plurality of electrodes 618 on a duty cycle based on a metabolization time of catecholamine. The duty cycle may include applying stimulation for 25% of a time period (e.g., minutes, hours, or days), and withhold stimulation for 75% the time period (e.g., minutes, hours, or days). The duty cycle control of delivery of the stimulation energy may reduce battery consumption of the controller 602. In addition, the stimulation energy may be delivered at a frequency between 2 Hz and 20 kHz. The stimulation energy may be applied as bursts of energy include pulses at a frequency between 2 Hz and 20 kHz, or continuously. In addition, the frequency and/or pulse width stimulation and/or current energy may also be altered continuously or periodically altered over time.

The stimulation energy delivered may be altered in response to patient 620 feedback based on the physical symptoms of the patient 620. Additionally, the controller 602 may instruct alteration of the stimulation energy provided to one or more of the plurality of electrodes 618 based on patient feedback. Therapy may be customized by calibrating to a target level of catecholamine release based on a change in physical symptoms or based on data obtained by the physiological sensor 606 and/or based on patient 620 or physician input on an external device, communicatively coupled with the controller 602, that may control the stimulation energy level. The patient 620 may be able to activate/deactivate therapy correlating to his/her own perceptions of their symptoms (e.g., when they feel symptoms of chronic fatigue, they may activate therapy). In these scenarios, the controller 602 may include a self-limiting mechanism to avoid depletion of catecholamines (e.g., the controller 602 down-regulates or turns off stimulation to after some period of time), so that a patient cannot cause depletion of catecholamines by requesting constant therapy.

The physiological sensor 606, in certain instances, may be configured to measure at least one physiological response of the patient 620. In addition to be being communicatively (and physically) coupled to the lead 604, the controller 602 may be communicatively coupled to the physiological sensor 606. The controller 602 may be configured to receive a signal from the physiological sensor 606 having data indicative of the at least one physiological response of the patient 620. Communication between the controller 602 and the physiological sensor 606 may be, or include, a wireless communication link such as, for example, a short-range radio link, such as Bluetooth, IEEE 802.11, a proprietary wireless protocol, and/or the like (as is described in further detail with reference to FIG. 2). The controller 602 may also analyze the signal from the physiological sensor 606 to calculate alteration of the stimulation energy, and communicate with the lead 604 to alter the stimulation energy based on analysis of the signal.

In certain instances, the physiological sensor 606 may be a separate sensor configured to receive physiological signals. In other instances, the physiological sensor 606 may be the controller 602 itself. Further, the physiological sensor 606 may be a remote implantable or wearable monitoring system (in communication with the controller 602). The physiological sensor 606 may also be a separate sensing lead that connects into the controller 602. The separate sensing lead may monitors signals from another target away from an adrenal gland 610 of a patient 620 to capture one or more physiological signals (e.g., indicative of blood pressure). The adrenal gland therapy system 600 may include one or more of these aspects as the physiological sensor 606.

In certain instances, the physiological sensor 606 may be configured to measure at least one of: heart rate of the patient 620, heart rate variability of the patient 620 (such as modulation in S1/S2 amplitudes with respiration), respiration rate of the patient 620, activity level of the patient 620, catecholamine levels of the patient 620 (e.g., chemosensor), metanephrine levels, metanephrine:creatinine (urine) ratio levels, metanephrine as a surrogate for plasma norepinephrine, body position, of the patient 620, body temperature of the patient 620, temperature of the adrenal gland 610, cardiac output of the patient 620, and arterial pressure of the patient 620, or any combination thereof (e.g., heart rate/respiration rate ratio). The activity level of the patient 620 may assist in informing the controller 602 whether stimulation energy should be altered (e.g., increased or blocked) due to an magnitude of change noted in the circulation and of circulating catecholamines. In certain instances, the physiological sensor 606 may be implanted in the bladder and determine the urine metanephrine levels of the patient 620, which is a surrogate for norepinephrine levels. A change in the above noted physiological responses may require a modulation the exocytosis or metabolization of catecholamines, for a resultant change in the physiological responses necessary. As a result, the controller 602 may alter (increase or decrease) the stimulation energy to alter modulate the release of catecholamines from the adrenal gland 610 to maintain a desired level of catecholamines in the patient 620.

In certain instances, the physiological sensor 606 may be configured to measure the body temperature of the patient 620. The physiological sensor 606 may also be configured to measure the cardiac output, stroke volume of the heart (e.g., S1 indicative of contractility or S2 as indicative of blood pressure changes due to sympathetic activity) contractility body of the heart, and/or mean arterial pressure/pulse pressures/systolic/diastolic of the patient 620 (via intra-arterial or peri-arterial approaches). The physiological sensor 606 may also measure other surrogates of catecholamine levels, or pain or non-pain symptoms of various disease states with neurohormonal or neurotransmitter dysfunction such as fibromyalgia (e.g., as indicated by exhaustion), chronic fatigue, sleep apnea, or the like. In certain instances, the physiological sensor 606 may be configured to measure surrogates of catecholamine levels associated with Postural Orthostatic Tachycardia Syndrome (POTS), orthostatic hypotension (OH), orthostatic intolerance (OI), or surrogates of catecholamine levels associated with heart failure and migraines, all which have a cause and effect due to changes in circulating catecholamine levels. The physiological sensor 606 may also measure decreased positive expiratory pressure (PEP), decreased raw left ventricular ejection time (LVET) and/or increased LVET corrected for heart rate. A change in the above note physiological responses may call for a modulation of the metabolization and exocytosis of catecholamines. As a result, the controller 602 may modulate the stimulation energy to modulate the release of catecholamines from the adrenal gland 610 to maintain a desired level of catecholamines in the patient 620.

The coordinated stimulation provided by the controller 602 may provide a closed-loop system which uses markers of systemic catecholamines or disease state to optimize therapy. In certain instances, two or more physiological parameters to provide the controller 602 with closed-loop control and enable predictive power to provide therapy only when needed or otherwise enabling improved therapy titration (e.g. stimulation amplitude, charge) and optimize clinical outcomes. To address either steady state deficiency or a transient deficiency (ability to ramp up/down quickly) of the adrenal gland 610 (or glands), the system 600 may use more than one physiological sensor 606 that communicate with the controller 602 as described above. The sensors may provide additional quantification, measurement, and tracking of the catecholamine levels or disease status as a function of activity to optimize therapy. The measurements of the various physiological sensors may be collected by the controller 602 and aggregated to alter delivery of the stimulation energy provided through the plurality of electrodes 618.

The physiological sensor 606 may measure the steady state deficiency of the catecholamines levels of the patient 620 by determining the physiological response measured by the physiological sensor 606 at a given steady state activity level. A transient deficiency may be monitored by looking at "transient" physiological sensor 606 measurements around activity state transition. In certain instances, a desirable response will be quick and more like an "underdamped" system with respect to maintaining the catecholamines levels of the patient 620, whereas a poor performance would look like an over-damped system. In certain instances, the controller 602 may be programmed based on patient customization. For example, a patient may prefer stimulation energy that is associated with lower systemic catecholamines. Thus, the controller 602 may program the stimulation to iterate in this manner. Another patient may prefer a state with higher systemic catecholamine, which would result in different stimulation energy (e.g., as compared to a patient that prefers lower systemic catecholamines). The controller 602 may be programmed with references within patients such that the stimulation energy may change based on activity level and time of day (awake/sleeping). Biomarker data could be used to calibrate the patients' preferences (increase or decrease) in systemic catecholamine levels in a closed loop system on a patient-by-patient basis.

As a specific example, the physiological sensor 606 may be configured to monitor heart rate activity. In the patient 620, the physiological sensor 606 may continuously record heart rate (HR) and activity (movement) information (e.g., using an accelerator), or body position (e.g., orthostatic imbalance) and parse the data stream into discrete activity bands. The time axes are separated in terms of transitions between the activity bands. HR data around the transitions may yield metrics for a transient deficiency, whereas HR data from in-between transitions and sufficiently away from the transitions may yield data for a steady state deficiency. In certain instances, in place of or along with monitoring the heart rate of the patient 620, the physiological sensor 606 may measure heart sounds. The heart sounds may provide an indication as to whether the patient 620 is awake or asleep to influence modulation of catecholamine levels. More specifically, when the patient 620 is sleeping, the controller 602 may be programmed to optimize (decrease) catecholamine levels to avoid insomnia by decreasing stimulation levels provided through the plurality of electrodes 618 as compared to when the patient is awake. The stimulation parameters may also be maintained to ensure catecholamine levels stay above a lower limit (low circulating catecholamine levels may be associated with a patient's current challenges with inability to sleep) or below an upper limit. in addition, when the patient 620 is exercising, the controller 602 may ensure optimal levels to reduce pain and fatigue (e.g., modulate levels based on baselines changes to exertion or stress) and ensure catecholamine levels stay above a lower limit (higher circulating levels may be associated with these patients' current challenges with lower tolerance for prolonged activity). As a result, the controller 602 may be configured to ensure appropriate modulation of catecholamine levels, which may vary when the patient is exercising, at rest or undergoing stressful experiences.

In certain instances, the plurality of electrodes 618 are stimulation elements configured to deliver stimulation energy therethrough. The stimulation elements 618 may be configured to deliver one or more of electrical stimulation, light stimulation, sound stimulation, thermal stimulation, and magnetic stimulation. In addition, the stimulation elements 618 may be configured to modulate release of L-dopa into a bloodstream of the patient. The stimulation elements 618 may be configured to stimulate the adrenal gland 610 (or glands) and facilitate release of L-dopa into the blood stream to maintain dopamine levels of the patient within a zone. Abnormal levels of L-dopa have been associated with degenerative diseases such as Parkinson's disease.

The controller 602, physically connected to the lead body 608 and electronically coupled to the plurality of stimulation elements 618, may be configured to instruct delivery of the stimulation energy through one or more of the plurality of stimulation elements 618 to modulate L-dopa release into the blood stream. Stimulation energy may be transmitted to the adrenal gland 610 in a monopolar or multipolar (e.g., bipolar, tripolar, etc.) fashion. Monopolar stimulation occurs when a selected one or more of the stimulation elements of the plurality of stimulation elements 618 is activated and transmits stimulation energy to tissue. Bipolar stimulation, a type of multipolar stimulation, occurs when two of the electrodes of the plurality of stimulation elements 618 are activated as anode and cathode, so that stimulation energy is transmitted between the activated stimulation elements. Multipolar stimulation also may occur when more than two (e.g., three, four, etc.) of the stimulation elements of the plurality of stimulation elements 618 are activated, e.g., two as anodes and a third as a cathode, two as cathodes and a third as an anode, and/or the like. In addition, the stimulation energy may be fractionalized across one or more of the electrodes of the plurality of stimulation elements 618. In certain instances, the level of L-dopa released, the amount of L-dopa in the blood stream, and/or the amount of dopamine in the patient associated with the released L-dopa may be sensed by the physiological sensor 606 and provided as feedback to the controller 602, which may alter the stimulation energy to achieve and/or maintain a desired L-dopa release level and/or a level of dopamine in the blood stream.

In certain instances, the controller may be configured to intermittently or continuously instruct delivery of the stimulation energy through different combinations of the one or more of the plurality of stimulation elements 618. In addition, the controller 602 may include circuitry (e.g., as described with reference to FIG. 1) that instructs delivery of the stimulation energy through one or more of the plurality of stimulation elements 618 on a duty cycle based on a metabolization time of L-dopa. Embodiments of the duty cycle may include, for example, applying stimulation for 25% of a time period (e.g., minutes, hours, or days), and withholding stimulation for 75% of the time period (e.g., minutes, hours, or days). The duty cycle control of delivery of the stimulation energy may reduce battery consumption of the controller 602. In addition, the stimulation energy may be delivered at a frequency between approximately 2 Hz and approximately 20 kHz. The stimulation energy may be applied as bursts of energy that include pulses at a frequency between approximately 2 Hz and approximately 20 kHz, or continuously. In addition, the frequency and/or pulse width stimulation and/or current energy may also be altered continuously or periodically over time.

The stimulation energy delivered may be altered in response to patient 620 feedback based on the physical symptoms of the patient 620. Additionally, the controller 602 may instruct alteration of the stimulation energy provided to one or more of the plurality of electrodes 618 based on patient feedback. Therapy may be customized by calibrating to a target level of L-dopa release based on a change in physical symptoms (e.g., tremors, muscle rigidity, and/or bradykinesia), based on data obtained by the physiological sensor 606, and/or based on patient 620 and/or physician input via an external device, communicatively coupled with the controller 602, that may control the stimulation energy level. The patient 620 may be able to activate/deactivate therapy correlating to his/her own perceptions of their symptoms (e.g., when they feel of tremors, they may activate therapy).

The physiological sensor 606, in certain instances, may be configured to measure at least one physiological response of the patient 620. In addition to being communicatively (and physically) coupled to the lead 604, the controller 602 may be communicatively coupled to the physiological sensor 606. The controller 602 may be configured to receive a signal from the physiological sensor 606 having data indicative of at least one physiological response of the patient 620. Communication between the controller 602 and the physiological sensor 606 may be, or include, a wireless communication link such as, for example, a short-range radio link, such as Bluetooth, IEEE 802.11, a proprietary wireless protocol, and/or the like (as is described in further detail with reference to FIG. 2). The controller 602 may also analyze the signal from the physiological sensor 606 to calculate alteration of the stimulation energy, and communicate with the lead 604 to alter the stimulation energy based on analysis of the signal.

In certain instances, the physiological sensor 606 may be a separate sensor configured to receive physiological signals. In other instances, the physiological sensor 606 may be the controller 602 itself. Further, the physiological sensor 606 may be a remote implantable or wearable monitoring system (in communication with the controller 602). The physiological sensor 606 may also be a separate sensing lead that connects into the controller 602. The separate sensing lead may monitor signals from another target away from an adrenal gland 610 of a patient 620 to capture one or more physiological signals (e.g., indicative of blood pressure). The adrenal gland therapy system 600 may include one or more of these aspects as the physiological sensor 606.

In certain instances, the physiological sensor 606 may be at least one of a vascular sensor configured to measure hypotension, a sensor configured to measure blood pressure of the patient, a bioimpedence sensor configured to measure blood pressure of the patient, an electoral sensor configured to assess vascular tone and/or heart pulse transit time, an optical sensor configured to assess vascular tone and/or heart pulse transit time, and an accelerometer configured to measure physical movement of the patient.

In certain instances, the plurality of simulation elements 618 may be configured to deliver stimulation energy to peripheral sympathetic nerves to modulate the release of L-dopa into the bloodstream. The lead 604 may be arranged to stimulate the peripheral sympathetic nerves rather than the adrenal gland 610, or, in embodiments, an addition lead 604 may be arranged to stimulate the peripheral sympathetic nerves along with a lead 604 stimulating the adrenal gland 610. In addition, a lead 614 may also be placed in the brain to provide stimulation energy for deep brain stimulation energy. This stimulation may also affect release of L-dopa.

The illustrative components shown in FIG. 6 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 1-5 may be, in embodiments, integrated with various other components depicted therein (and/or components not illustrated), all of which are considered to be within the ambit of the disclosed subject matter. For example, the adrenal gland stimulation lead 602 may be used in connection with the systems described with reference to FIG. 1 and FIG. 2. In addition, the adrenal gland stimulation lead 604 may include the helical anchors 312 as shown in FIG. 3, or the thermoelectric element 410 or the paddle component 404 as shown in FIG. 4.

Figure 7A:
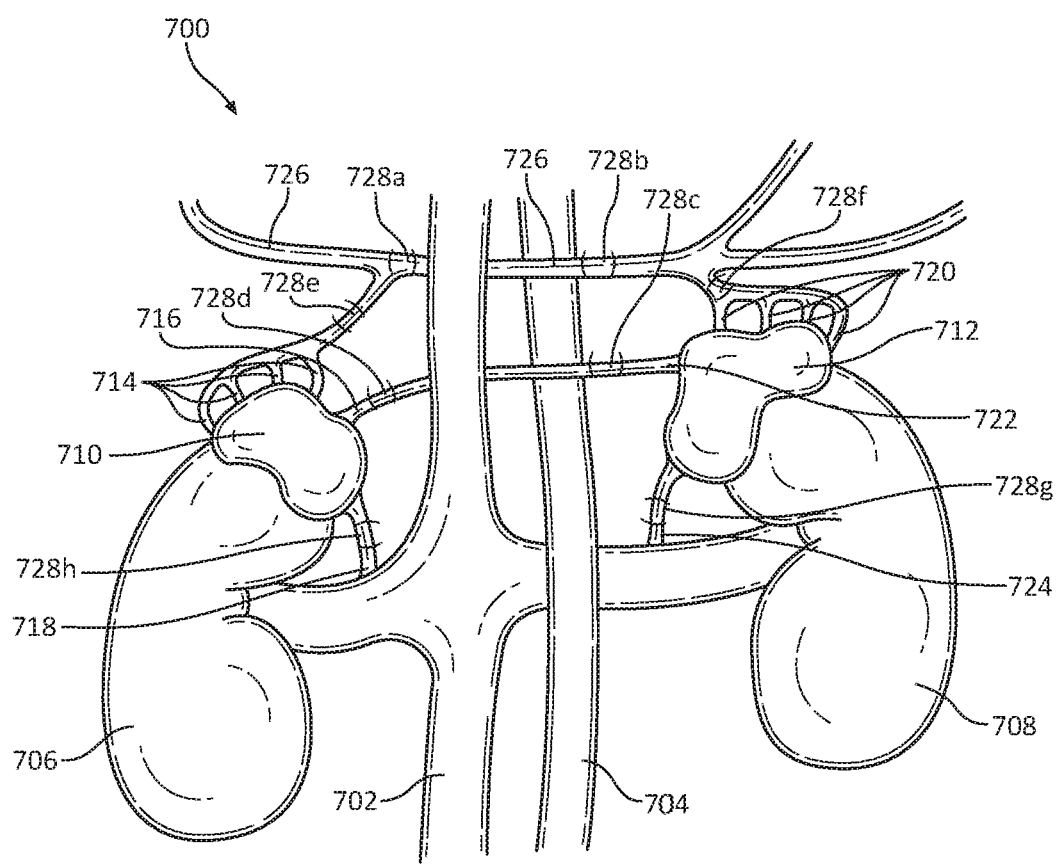
FIG. 7A is an example illustration of another adrenal gland therapy system in accordance with embodiments of the disclosure.
Figure 7B:
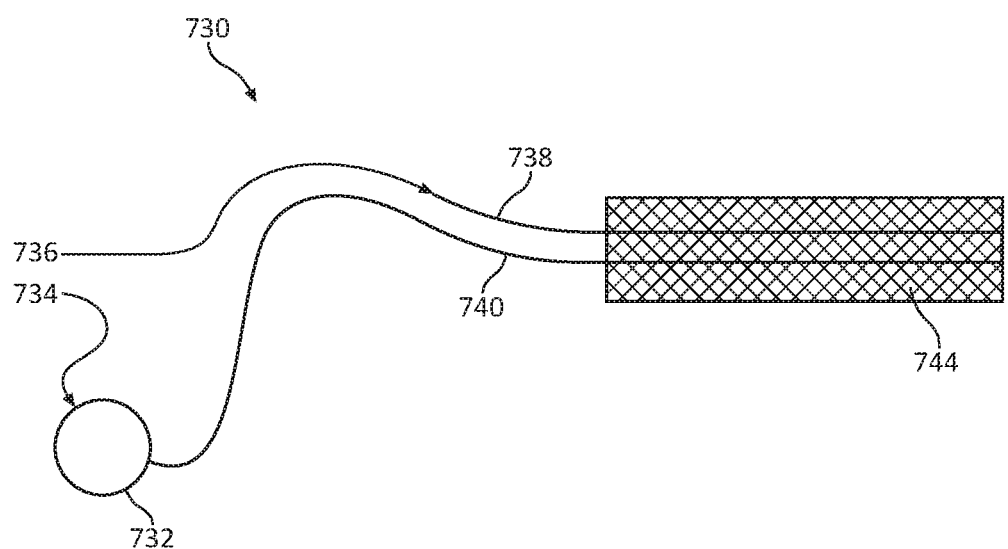
FIG. 7B is an example illustration of a thermoelectric element included with the adrenal gland therapy system shown in FIG. 7A in accordance with embodiments of the disclosure.

FIG. 7A is an example illustration of another adrenal gland therapy system in accordance with embodiments of the disclosure. FIG. 7 shows various aspects of the anatomy 700 in a patient including the aorta 704, the vena cava 702, the right kidney 706, the left kidney 708, the right adrenal gland 710, and the left adrenal gland 712. Certain aspects of the vasculature are also highlighted including the right superior suprarenal arteries 714, right middle suprarenal artery 716, right inferior suprarenal artery 718, left superior suprarenal arteries 720, left middle suprarenal artery 722, left inferior suprarenal artery 724, and the right and left interior phrenic arteries 726. The adrenal gland therapy system may include attaching or coupling a thermoelectric element (shown in FIG. 7B) to one or more locations 728*a-h* of the vasculature. The thermoelectric element may cool one or both of the adrenal glands 710, 712 to modulate catecholamine release from chromaffin cells therein.

FIG. 7B is an example illustration of a cooling system 730 included with the adrenal gland therapy system shown in FIG. 7A in accordance with embodiments of the disclosure. The cooling system 730 may be attached to one or more locations 728*a-h* shown in FIG. 7A. At the locations 728*a-h*, the cooling system 730 cools blood flow into the adrenal glands 710, 712. Cooling the blood may cool the periglandular region of the adrenal glands 710, 712, which may trigger catecholamine release from chromaffin cells within the adrenal glands 710, 712. As a result, the cooling system 730 may have a resultant effect of increasing the circulating levels of norepinephrine and dopamine within the bloodstream, similar to stimulation of the adrenal glands 710, 712. The cooling system 730 may be used alone or in combination with the stimulation systems or leads discussed herein (e.g., FIGS. 1-6). More specifically, the cooling system 730 may include a controller 732. The controller 732 may apply current to apply the cooling effect. The controller 732 may also be coupled to adrenal gland stimulation leads, as discussed herein (e.g., FIGS. 1-6), to control stimulation applied to the adrenal glands 710, 712. The controller 732 may apply cooling and stimulation concurrently, or alternate cooling and stimulation. This may increase the battery life of the controller 732 by reducing battery consumption and may also reduce chances of attenuated effectiveness over time due to adaptation or depletion of the adrenal glands 710, 712.

The cooling system 730 may include at least one thermoelectric element (e.g., a Peltier element) to effect cooling of the adrenal gland 710, 712. As shown in FIG. 7B, a stent or wrap 744 is arranged at one of the locations 728*a-h* of the vasculature in or around an artery. In certain instances, the stent or wrap 744 may be arranged directly on one or both of the adrenal glands 710, 712. The stent or wrap 744 includes a thermoelectric element that is coupled to the controller 730 via insulated wires 738, 740. The controller 732 may apply current 734, 736 via the insulated wires 738, 740, and dissipate heat that results from the thermoelectric element. The cooling system 730 may supply a cooling at a temperature range from 4 degrees Celsius to 32 degrees Celsius.

The illustrative components shown in FIGS. 7A-B are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 7A-B may be, in embodiments, integrated with various other components depicted therein (and/or components not illustrated), all of which are considered to be within the ambit of the disclosed subject matter. For example, the cooling system 730 may be used in connection with the systems described with reference to FIG. 1 and FIG. 2 or the adrenal gland stimulation leads and systems described with reference to FIGS. 3-6.

Figure 8:
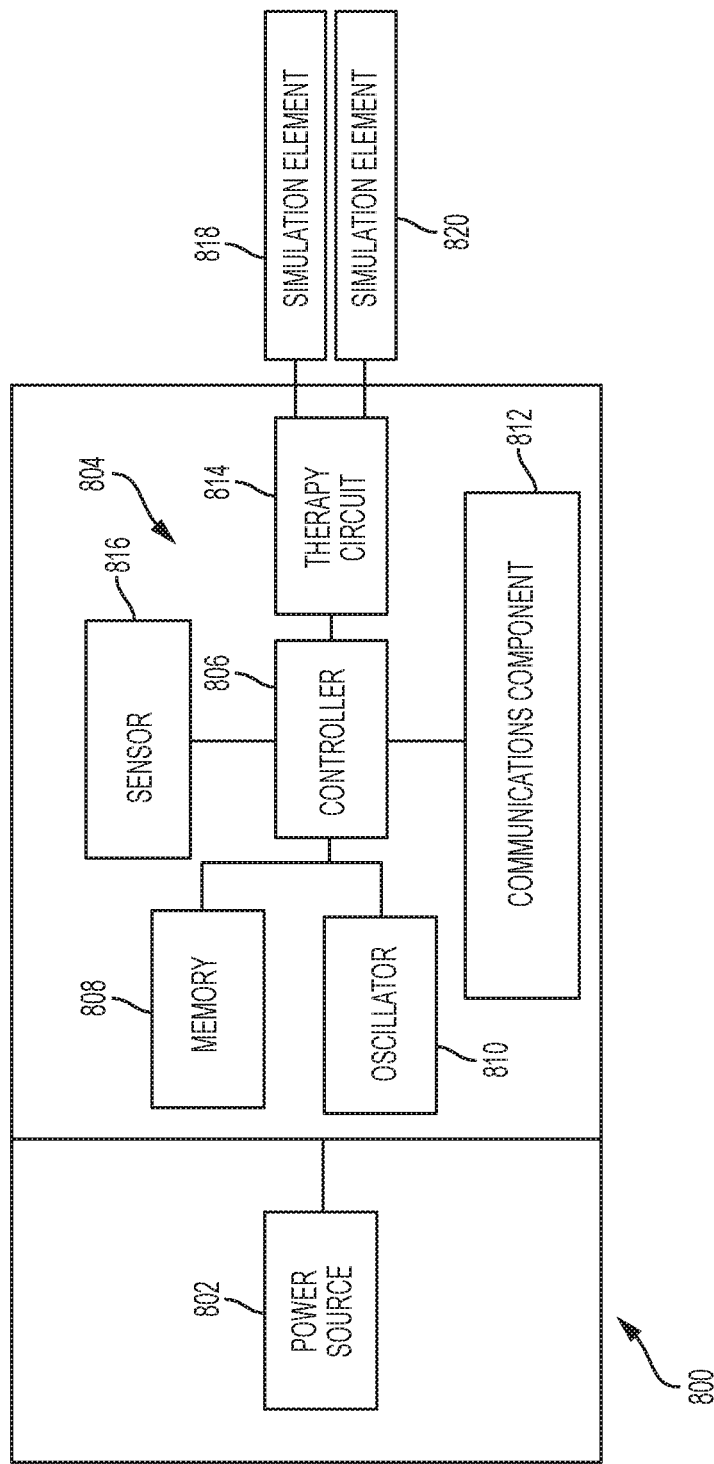
FIG. 8 is a schematic block diagram of a leadless implantable medical device, in accordance with aspects of embodiments of the disclosure.

FIG. 8 is a schematic block diagram of a leadless implantable medical device (IMD) 800, in accordance with aspects of embodiments of the disclosure. As shown in FIG. 8, the leadless implantable medical device 800 includes a power source 802 that powers operational circuitry 804 of the leadless implantable medical device 800. The operational circuitry 804 includes a controller 806 coupled to a memory 808. An oscillator 810 coupled to the controller 806 may be used as a clocking mechanism to provide timing functions to the controller 806. In certain instances, other types of clocking mechanisms may be used instead of, as well as, or in addition to, the oscillator 810. The operational circuitry 804 also includes a communications component 812, a therapy circuit 814, and a physiological sensor 816. As shown in FIG. 3, the therapy circuit 814 is coupled to stimulation elements 818 and 820 and is configured to provide stimulation energy to the stimulation elements 818 and 820, which, in turn, provide the energy to a patient's adrenal gland. The IMD 800 may include more than two stimulation elements 818 and 820. The stimulation elements 818 and 820 may be configured to modulate release of L-dopa. Additionally, the communications component 812 may include a transceiver and/or an antenna.

The IMD 800 may also include a sensor 816 configured to sense and facilitate analysis of L-dopa levels within the patient, L-dopa release, and/or dopamine levels within the patient that are associated with L-dopa. The sensor 816 may be, for example, a vascular sensor configured to measure hypotension, a sensor configured to measure blood pressure of the patient, a bioimpedence sensor configured to measure blood pressure of the patient, an electoral sensor configured to assess vascular tone or heart pulse transit time, an optical sensor configured to assess vascular tone or heart pulse transit time, an accelerometer configured to measure physical movement of the patient, and/or the like.

Figure 9:
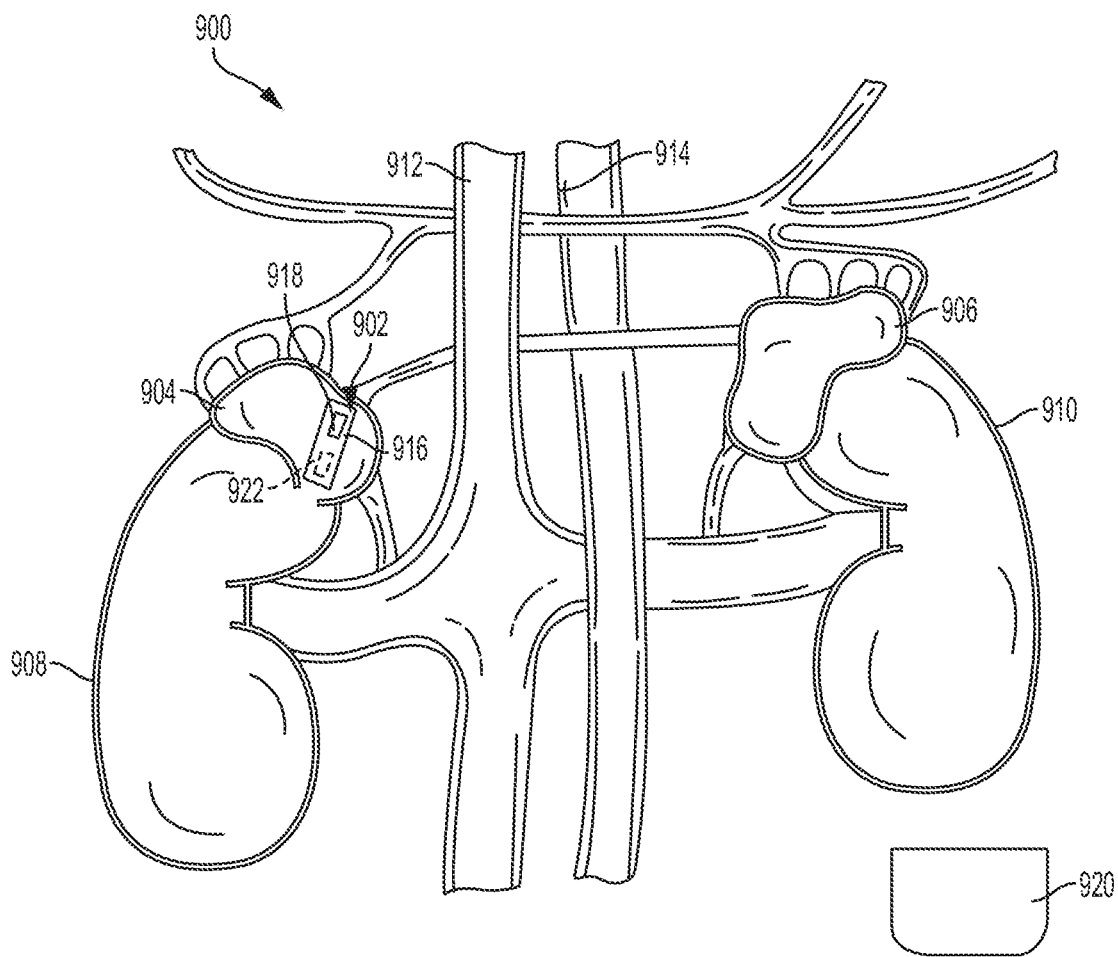
FIG. 9 is a schematic illustration of an implantable system including an implantable medical device (IMD) attached to a portion of a patient's adrenal gland in accordance with embodiments of the present disclosure.

FIG. 9 is a schematic illustration of a portion of a patient's anatomy 900 and an associated implantable system including an implantable medical device (IMD) 902 attached to a portion of a patient's adrenal gland 904, in accordance with embodiments of the present disclosure. The anatomy 900 shown in FIG. 9 includes adrenal glands 904, 906 (with Gerota's fascia), which are located above the patient's kidneys 908, 910, which are located on either side of the patient's vena cava 912 and aorta 914. The IMD 902 may include a leadless body housing 916 configured to engage the adrenal gland 904 (and/or periadrenal connective tissue), and at least one stimulation element 918 arranged with the leadless body housing 916. The leadless body housing 916 may also be attached adjacent to one or both of the adrenal glands 904, 906 (e.g., within the retroperitoneal space such as the peritoneum or submuscular region (i.e. Longissimus muscles) above the adrenal glands 904, 906). The stimulation element 918 may be configured to deliver stimulation energy to modulate release of L-dopa into a bloodstream of the patient. In certain instances, the stimulation element 918 may be configured to stimulate the adrenal gland 904 (or glands) and release of L-dopa into the blood stream to maintain dopamine levels of the patient within a zone.

In certain instances, the stimulation element 918 is configured to deliver electrical stimulation, light stimulation, sound stimulation, thermal stimulation, and/or magnetic stimulation to the adrenal gland 904 to modulate L-dopa release. The stimulation element 918 may be specifically configured to deliver the intended type of stimulation energy. The stimulation element 918 may be configured to facilitate release of L-dopa into the systemic circulation, which may lessen physical symptoms of the patient in neurodegenerative diseases. L-dopa release may lessen at least one of tremors, muscle rigidity, and bradykinesia of the patient. The stimulation and modulation may be used to keep dopamine (as a certain portion of L-dopa may be converted prior to crossing the blood-brain-barrier) levels within a certain safety zone to mitigate blood pressure and/or other physical effects and, in embodiments, may be based upon individual clinical signs. The IMD 902 may communicate with a controller 920 to effect stimulation through the stimulation element 918.

As shown in FIG. 9, the IMD 902 is a wireless electrode stimulator assembly with the controller 920 configured to communicate with the IMD 902. In certain instances, the controller 920 may be co-implanted and may provide therapy and/or diagnostic data about the patient and/or the controller 920. In other instances, the controller 920 may be arranged external to the patient. The IMD 902 may include circuitry to sense and analyze the adrenal gland 904 electrical activity, and to determine if and when a pacing electrical pulse needs to be delivered and, in instances having multiple IMDs 902 (e.g., an IMD attached to adrenal gland 904), to determine which of the IMDs 902 should deliver the pulse. The controller 920 may have one or more sensors 922 (e.g., as described above with reference to FIG. 8). The sensor or sensors 922 may also be arranged with the leadless body housing 916. The aldosterone levels of the patient may be sensed by the sensor 922 and provided as feedback to the controller 920, which may alter the stimulation energy to achieve desired aldosterone levels of the patient.

The controller 902 may be configured to analyze the signal from the sensor 922 to calculate alteration of the stimulation energy, and alter the stimulation energy based on analysis of the signal. The data indicative of the L-dopa release levels of the patient may be measured by the sensor 922 of the controller 920 and/or leadless body housing 916, which may be a vascular sensor 922 configured to measure hypotension, a sensor 922 configured to measure blood pressure of the patient, a bioimpedence sensor 922 configured to measure blood pressure of the patient, an electoral sensor 922 configured to assess vascular tone or heart pulse transit time, an optical sensor 922 configured to assess vascular tone or heart pulse transit time, an accelerometer configured to measure physical movement of the patient, and/or the like.

In certain instances, the IMD 902 has an internal receiver that may receive communications and/or energy from the controller 920, which may include a transmitter. The controller 920 may include a pulse generator that supplies an appropriate time-varying energy (e.g., current or voltage) to the IMD 902. The IMD 902 may include a power source for storing electrical energy, and may also have a triggering mechanism to deliver stored energy to the adrenal gland via the stimulation element 918. The IMD 902 may be a passive stimulator such that stimulation energy is transmitted via the controller 920, stored with the IMD 902, and stimulated in response to a prompt from the controller 920. In other instances, the IMD 902 may be an active stimulator and provide stimulation based on control circuitry contained therein (e.g., as described in further detail in FIG. 8).

Any number of a variety of communication methods and protocols may be used, via communication links, to facilitate communication between devices in the adrenal gland therapy system discussed herein. For example, wired and/or wireless communications methods may be used. Wired communication methods may include, for example and without limitation, traditional copper-line communications such as DSL, broadband technologies such as ISDN and cable modems, and fiber optics, while wireless communications may include cellular communications, satellite communications, radio frequency (RF) communications, infrared communications, induction, conduction, acoustic communications, and/or the like.

Modulation of aldosterone, consistent with the various aspects of the present disclosure, may be non-hemodynamic. Modulation can encompass a slow rise or abrupt rise. Blunting may have abrupt compensatory rise after stimulation turned off, or may have residual blunting effects prior to plasma rise after stimulation turned off. The discovery of using electrical stimulation to modulate aldosterone levels (as opposed to use of pharmaceutical drugs) was unexpected as stimulation was not thought to interact, affect, nor disrupt the RAAS as noted above.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method of delivering therapy to an adrenal gland of a patient, the method comprising:
    delivering a housing to an implant location between a capsule and the adrenal gland of the patient, the housing including a plurality of stimulation elements arranged with the housing; and
    delivering stimulation energy through at least one of the plurality of stimulation elements to modulate aldosterone levels within the patient.

2. The method of claim 1, further comprising delivering stimulation energy to peripheral sympathetic nerves to modulate a release of L-dopa into the bloodstream.

3. The method of claim 1, further comprising delivering deep brain stimulation energy to the patient delivering stimulation energy.

4. The method of claim 1, further comprising measuring a physical symptom of the patient associated with Parkinson's disease and altering delivery of the stimulation energy in response thereto.

5. The method of claim 1, wherein the plurality of stimulation elements are configured to deliver at least one of electrical stimulation, light stimulation, sound stimulation, thermal stimulation, and magnetic stimulation to the adrenal gland to modulate a release of naturally occurring L-dopa.

6. The method of claim 1, further comprising a sensor configured to measure the naturally occurring L-dopa levels within the patient and alter the stimulation energy delivered through the at least one of the plurality of stimulation elements to maintain the naturally occurring L-dopa release within a zone.

7. The method of claim 6, wherein the sensor is at least one of a vascular sensor configured to measure hypotension, a sensor configured to measure blood pressure of the patient, a bioimpedence sensor configured to measure blood pressure of the patient, an electoral sensor configured to assess vascular tone or heart pulse transit time, an optical sensor configured to assess vascular tone or heart pulse transit time, and an accelerometer configured to measure physical movement of the patient.

8. The method of claim 7, wherein the housing comprises a communications component configured to communicate wireless signals, and the sensor is configured to measure dopamine levels associated with naturally occurring L-dopa within the patient and communicate feedback to the communications component via wireless signals to alter the stimulation energy delivered through the at least one of the plurality of stimulation elements to maintain the naturally occurring L-dopa release within a zone.

9. The method of claim 1, wherein the plurality of stimulation elements are configured to deliver stimulation energy according to a duty cycle that is based on a metabolization time of naturally occurring L-dopa within the patient.

10. The method of claim 1, wherein the delivery of stimulation energy modulates release of naturally occurring L-dopa to lessen at least one of tremors, muscle rigidity, and bradykinesia of the patient.

11. The method of claim 1, wherein the plurality of stimulation elements are configured to intermittently or continuously instruct delivery of the stimulation energy through the plurality of stimulation elements.

* * * * *